US009040551B2

(12) United States Patent
Weinfeld et al.

(10) Patent No.: US 9,040,551 B2
(45) Date of Patent: May 26, 2015

(54) SMALL MOLECULE INHIBITORS OF POLYNUCLEOTIDE KINASE/PHOSPHATASE, POLY(ADP-RIBOSE) POLYMERASE AND USES THEREOF

(75) Inventors: Michael Weinfeld, Edmonton (CA); Dennis G. Hall, Edmonton (CA); Feridoun Karimi-Busheri, Edmonton (CA); Gary Kenneth Freschauf, Edmonton (CA); Todd Randall Mereniuk, St. Albert (CA)

(73) Assignees: THE GOVERNORS OF THE UNIVERSITY OF ALBERTA, Alberta (CA); ALBERTA HEALTH SERVICES, Alberta (CA)

( * ) Notice: Subject to any disclaimer, the term of this patent is extended or adjusted under 35 U.S.C. 154(b) by 687 days.

(21) Appl. No.: 13/375,876

(22) PCT Filed: Jun. 4, 2010

(86) PCT No.: PCT/CA2010/000846
§ 371 (c)(1),
(2), (4) Date: Feb. 20, 2012

(87) PCT Pub. No.: WO2010/139069
PCT Pub. Date: Dec. 9, 2010

(65) Prior Publication Data
US 2012/0142721 A1 Jun. 7, 2012

Related U.S. Application Data

(60) Provisional application No. 61/184,013, filed on Jun. 4, 2009, provisional application No. 61/263,711, filed on Nov. 23, 2009.

(51) Int. Cl.
| | | |
|---|---|---|
| A61K 31/437 | (2006.01) | |
| A61K 31/4375 | (2006.01) | |
| C07D 471/04 | (2006.01) | |
| A61N 5/10 | (2006.01) | |
| A61K 31/4745 | (2006.01) | |

(52) U.S. Cl.
CPC .............. *A61N 5/10* (2013.01); *A61K 31/4375* (2013.01); *A61K 31/437* (2013.01); *A61K 31/4745* (2013.01); *A61N 2005/1098* (2013.01); *C07D 471/04* (2013.01)

(58) Field of Classification Search
CPC . A61K 31/437; A61K 31/4375; C07D 471/04
USPC .................. 514/283, 300; 546/113
See application file for complete search history.

(56) References Cited

FOREIGN PATENT DOCUMENTS

WO     2009/007677 A2     1/2009

OTHER PUBLICATIONS

International Search Report issued in PCT/CA2010/000846 on Sep. 22, 2010.
Written Opinion issued in PCT/CA2010/000846 on Sep. 22, 2010.
Freschauf et al., Mechanism of Action of an Imidopiperidine Inhibitor of Human Polynucleotide Kinase/Phosphatase, The Journal of Biological Chemistry, 285(4): 2351-2360, 2010.
Roasouli-Nia et al., Stable down-regulation of human polynucleotide kinase enhances spontaneous mutation frequency and sensitizes cells to genotoxic agents, PNAS, 101(18):6905-6910, 2004.
Ulaczyk-Lesanko et al., Optimization of three- and four-component reactions for polysubstituted piperidines: application to the synthesis and preliminary biological screening of a prototype library, J Comb Chem, 9(4):695-703, 2007—Abstract Only.
Madhusudan and Middleton, The emerging role of DNA repair proteins as predictive, prognostic and therapeutic targets in cancer. Cancer Treat Rev. Dec. 2005;31(8):603-617.
O'Connor et al., Targeted cancer therapies based on the inhibition of DNA strand break repair. Oncogene. Dec. 10, 2007;26(56):7816-7824.
Drew and Calvert, The Potential of PARP Inhibitors in Genetic Breast and Ovarian Cancers. Ann N Y Acad Sci. Sep. 2008;1138:136-145.
Madhusudan et al., Isolation of a small molecule inhibitor of DNA base excision repair. Nucleic Acids Res. Aug. 19, 2005;33(15):4711-4724.
Marchand et al., Identification of phosphotyrosine mimetic inhibitors of human tyrosyl-DNA phosphodiesterase I by a novel AlphaScreen high-throughput assay. Mol Cancer Ther. Jan. 2009;8(1):240-248.
Hickson et al., Identification and Characterization of a Novel and Specific Inhibitor of the Ataxia-Telangiectasia Mutated Kinase ATM. Cancer Res. Dec. 15, 2004;64(24):9152-9159.
Zhao et al., Preclinical Evaluation of a Potent Novel DNA-Dependent Protein Kinase Inhibitor NU7441. Cancer Res. May 15, 2006;66(10):5354-5362.
Plummer et al., Phase I study of the Poly(ADP-Ribose) Polymerase Inhibitor, AG014699, in Combination with Temozolomide in Patients With Advanced Solid Tumors. Clin Cancer Res 2008;14(23):7917-7923.

(Continued)

*Primary Examiner* — Raymond Henley, III
(74) *Attorney, Agent, or Firm* — Michael A. Whittaker; Acuity Law Group, P.C.

(57) ABSTRACT

The present invention generally relates to use of compounds and compositions as a chemosensitizers and/or radiosensitizers and/or inhibitors of PNKP phosphatase activity. The present invention provides pharmaceutical combinations and/or a pharmaceutically acceptable salt thereof, kits containing such compounds and/composition and methods of using such compounds and/or compositions.

13 Claims, 17 Drawing Sheets

(56) References Cited

OTHER PUBLICATIONS

Henner et al., Gamma Ray Induced Deoxyribonucleic Acid Strand Breaks. J Biol Chem. Jan. 25, 1983;258(2):711-713.

Lennartz et al., Oxygen-effect on strand breaks and specific end-groups in DNA of irradiated thymocytes. Int J Radiat Biol Relat Stud Phys Chem Med. Jun. 1975;27(6):577-587.

Friedberg et al., DNA Repair and Mutagenesis. 2nd ed. Washington, D.C.: ASM Press; 2006:204-205.

Krokan et al., Base excision repair of DNA in mammalian cells. FEBS Lett. Jun. 30, 2000;476(1-2):73-77.

Jilani et al., Molecular Cloning of the Human Gene, PNKP, Encoding a Polynucleotide Kinase 3'-Phosphatase and Evidence for Its Role in Repair of DNA Strand Breaks Caused by Oxidative Damage. J Biol Chem. Aug. 20, 1999;274(34):24176-24186.

Karimi-Busheri et al., Molecular Characterization of a Human DNA Kinase. J Biol Chem. Aug. 20, 1999;274(34):24187-24194.

Whitehouse et al., XRCCI Stimulates Human Polynucleotide Kinase Activity at Damaged DNA Termini and Accelerates DNA Single-Strand Break Repair. Cell. Jan. 12, 2001;104(1):107-117.

Loizou et al., The Protein Kinase CK2 Facilitates Repair of Chromosomal DNA Single-Strand Breaks. Cell. Apr. 2, 2004;117(1):17-28.

Mani et al., XRCCI Stimulates Polynucleotide Kinase by Enhancing Its Damage Discrimination and Displacement from DNA Repair Intermediates. J Biol Chem. Sep. 21, 2007;282(38):28004-28013.

Chappell et al., Involvement of human polynucleotide kinase in double-strand break repair by non-homologous end joining. EMBO J. Jun. 3, 2002;21(11):2827-2832.

Koch et al., Xrcc4 physically links DNA end processing by polynucleotide kinase to DNA ligation by DNA ligase IV. EMBO J. Oct. 1, 2004;23(19):3874-3885.

Karimi-Busheri et al., Human Polynucleotide Kinase Participates in Repair of DNA Double-Strand Breaks by Nonhomologous End Joining but not Homologous Recombination. Cancer Res. Jul. 15, 2007;67(14):6619-6625.

Wiederhold et al., AP Endonuclease-Independent DNA Base Excision Repair in Human Cells. Mol Cell. Jul. 23, 2004;15(2):209-220.

Das et al., NEIL2-initiated, APE-independent repair of oxidized bases in DNA: Evidence for a repair complex in human cells. DNA Repair (Amst). Dec. 9, 2006;5(12):1439-1448.

PLO et al, Association of XRCC1 and tyrosyl DNA phosphodiesterase (Tdp1) for the repair of topoisomerase I-mediated DNA lesions. DNA Repair (Amst). Oct. 7, 2003;2(10):1087-1100.

Rasouli-Nia et al., Stable down-regulation of human polynucleotide kinase enhances spontaneous mutation frequency and sensitizes cells to genotoxic agents. Proc Natl Acad Sci U S A. May 4, 2004;101(18):6905-6910.

Bernstein et al., The Molecular Architecture of the Mammalian DNA Repair Enzyme, Polynucleotide Kinase. Mol Cell. Mar. 4, 2005;17(5):657-670.

Dobson and Allinson, The phosphatase activity of mammalian polynucleotide kinase takes precedence over its kinase activity in repair of single strand breaks. Nucleic Acids Res. Apr. 28, 2006;34(8):2230-2237.

Bernstein et al., Polynucleotide kinase as a potential target for enhancing cytotoxicity by ionizing radiation and topoisomerase I inhibitors. Anticancer Agents Med Chem. May 2008;8(4):358-367.

Ulaczyk-Lesanko et al., Optimization of Three-and Four-Component Reactions for Polysubstituted Piperidines: Application to the Synthesis and Preliminary Biological Screening of a Prototype Library. J Comb Chem. Jul.-Aug. 2007;9(4):695-703.

Mani et al., Spectroscopic Studies of DNA and ATP Binding to Human Polynucleotide Kinase: Evidence for a Ternary Complex. Biochemistry. Oct. 21, 2003;42(41):12077-12084.

Meijer et al., Pnk1, a DNA Kinase/Phosphatase Required for Normal Response to DNA Damage by Gamma-Radiation or Camptothecin in *Schizosaccharomyces pombe*. J Biol Chem. Feb. 8, 2002;277(6):4050-4055.

Misik et al., Protein Phosphatase Regulation of Na+/H+ Exchanger Isoform I. Biochemistry. Apr. 19, 2005;44(15):5842-5852.

Wei and Lee, Expression and Reconstitution of Calcineurin A and B Subunits. Biochem Mol Biol Int. Jan. 1997;41(1):169-177.

An and Carmichael, Use of a colorimetric protein phosphatase inhibition assay and enzyme linked immunosorbent assay for the study of microcystins and nodularins. Toxicon. Dec. 1994;32(12):1495-1507.

Rininsland et al., Metal ion-mediated polymer superquenching for highly sensitive detection of kinase and phosphatase activities. Proc Natl Acad Sci U S A. Oct. 26, 2004;101(43):15295-15300.

Karimi-Busheri et al., Repair of DNA strand gaps and nicks containing 3'-phosphate and 5'-hydroxyl termini by purified mammalian enzymes. Nucleic Acids Res. Oct. 1, 1998;26(19):4395-4400.

Aravind and Koonin, The HD domain defines a new superfamily of metal-dependent phosphohydrolases. Trends Biochem Sci. Dec. 1998;23(12):469-472.

Wang et al., Structure and mechanism of T4 polynucleotide kinase: an RNA repair enzyme. EMBO J. Jul. 15, 2002;21(14):3873-3880.

Villafranca et al., Protein serine/threonine phosphatases. Curr Opin Biotechnol. Aug. 1996;7(4):397-402.

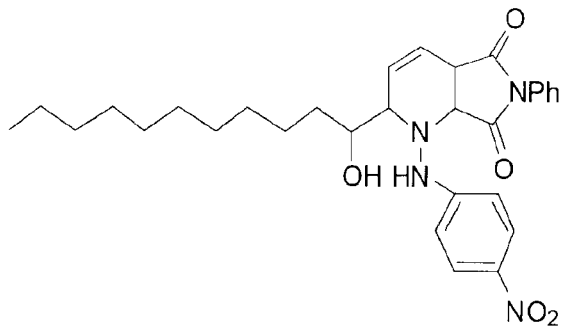

A12B4C3
2-(1-hydroxyundecyl)-1-(4-nitrophenylamino)-6-phenyl-6,7a-dihydro-1H-pyrrolo[3,4-b]pyridine-5,7(2H,4aH)-dione

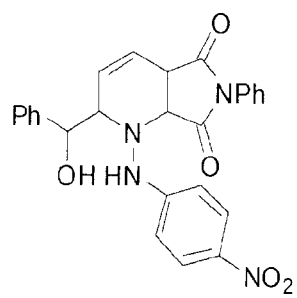

A1B4C3
2-(hydroxy(phenyl)methyl)-1-(4-nitrophenylamino)-6-phenyl-6,7a-dihydro-1H-pyrrolo[3,4-b]pyridine-5,7(2H,4aH)-dione

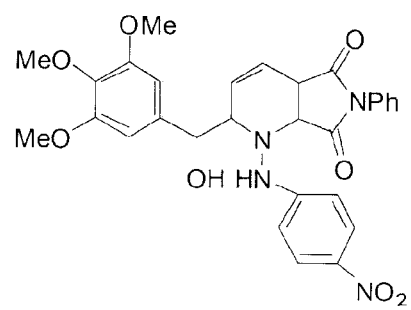

A6B4C3
2-(hydroxy(3,4,5-trimethoxyphenyl)methyl)-1-(4-nitrophenylamino)-6-phenyl-6,7a-dihydro-1H-pyrrolo[3,4-b]pyridine-5,7(2H,4aH)-dione

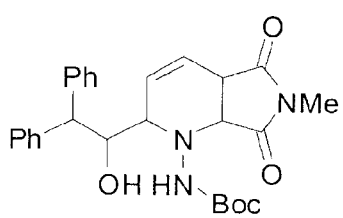

A26B11C2
tert-butyl 2-(1-hydroxy-2,2-diphenylethyl)-6-methyl-5,7-dioxo-2,4a,5,6,7,7a-hexahydro-1H-pyrrolo[3,4-b]pyridin-1-ylcarbamate

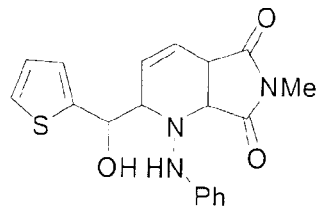

A39B1C2
2-(hydroxy(thiophen-2-yl)methyl)-6-methyl-1-(phenylamino)-6,7a-dihydro-1H-pyrrolo[3,4-b]pyridine-5,7(2H,4aH)-dione

Figure 2

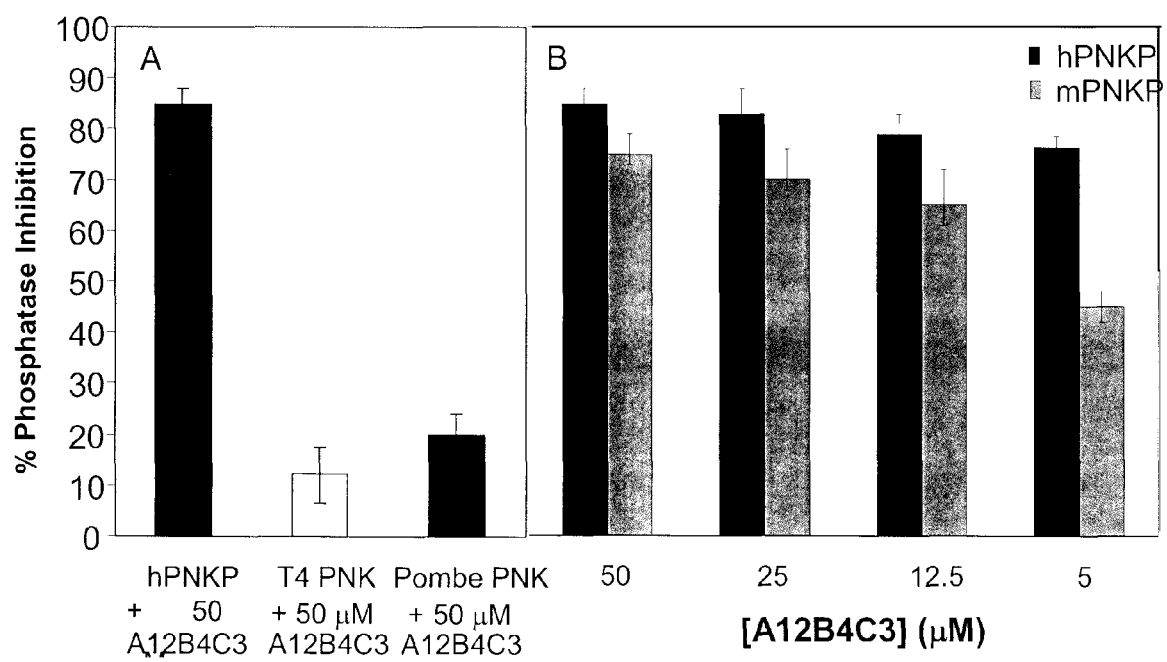
Figure 5A & B

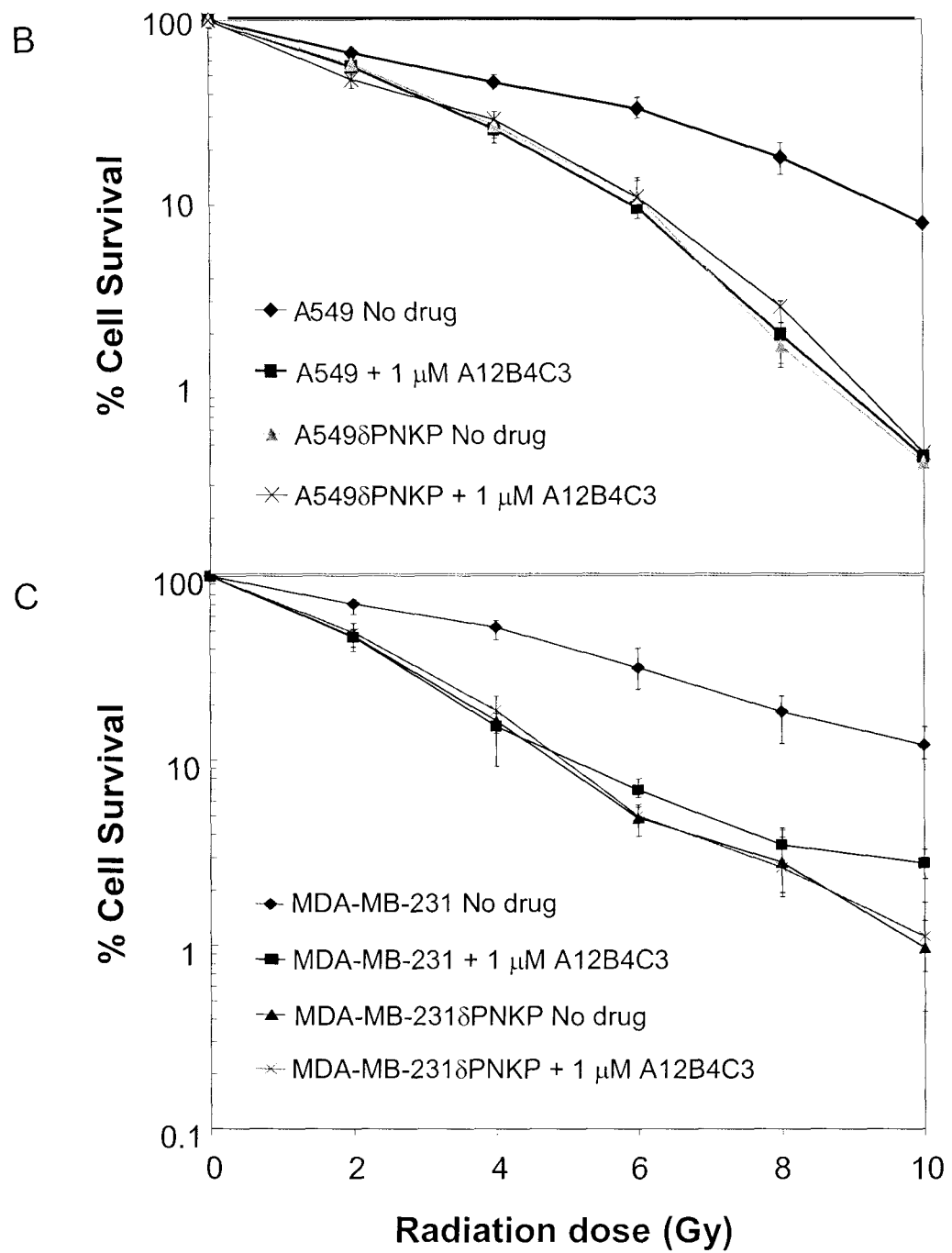
Figures 6B & C

US 9,040,551 B2

SMALL MOLECULE INHIBITORS OF POLYNUCLEOTIDE KINASE/PHOSPHATASE, POLY(ADP-RIBOSE) POLYMERASE AND USES THEREOF

RELATED APPLICATIONS

This application is filed under 35 U.S.C. §371 as the U.S. national phase of International Application No. PCT/CA2010/000846, filed Jun. 4, 2010, which designated the U.S. and claims the benefit of priority to U.S. Provisional Application Ser. No. 61/184,013, filed Jun. 4, 2009, and to U.S. Provisional Application Ser. No. 61/263,711, filed Nov. 23, 2009, each of which is hereby incorporated in its entirety including all tables, figures, and claims.

FIELD OF THE INVENTION

The field of the invention generally relates to inhibitors of polynucleotide kinase/phosphatase and poly(ADP-ribose) polymerase, and their compounds, compositions, methods and kits and uses thereof.

BACKGROUND OF THE INVENTION

Radiation and systemic chemotherapy are important therapeutic modalities for the treatment of cancer. Nuclear DNA is considered to be a major cellular target responsible for the cytotoxicity of ionizing radiation and many conventional antineoplastic drugs. As a consequence, the levels of DNA damage and its repair are likely to influence cell survival and affect clinical outcome (1).

The manipulation of DNA repair systems has recently become the focus of considerable interest as a means of enhancing the efficacy of radio- and chemotherapy. Particular emphasis has been placed on single and double-strand break repair pathways (2). Small molecule inhibitors have now been developed that target enzymes such as poly(ADP-ribose) polymerase (PARP) and apurinic/apyrimidinic endonuclease (APE 1), which are involved in the repair of damaged bases and single-strand breaks induced by many agents including ionizing radiation and alkylating agents (1, 3, 4); tyrosyl DNA-phosphodiesterase (Tdp1), which is required for the repair of strand breaks introduced by topoisomerase 1 inhibitors such as camptothecin and irinotecan (5); and ATM and DNA-PK, which regulate the response to DNA double-strand breaks (6, 7). Inhibitors of PARP are now in clinical trial (8).

Ionizing radiation and other genotoxic agents often generate strand breaks with incompatible termini that must be processed in order for single and double-strand break repair pathways to complete the repair. Among the frequently observed termini are 3'-phosphate and phosphoglycolate and 5'-hydroxyl groups (9, 10). These lesions create a barrier for DNA polymerases and ligases to replace missing bases and seal the breaks because these enzymes have a strict requirement for the presence of a 3'-hydroxyl group and in addition DNA ligases require a 5'-phosphate group (11, 12).

A major enzyme responsible for the phosphorylation of 5'-hydroxyl termini and dephosphorylation of 3'-phosphate termini in human cells is polynucleotide kinase/phosphatase (hPNKP) (13, 14). In the single-strand break (SSB) repair pathway hPNKP acts in concert with XRCC1, DNA polymerase β and DNA ligase III (15-17). PNKP-mediated DNA end-processing at double-strand breaks is a component of the nonhomologous end-joining (NHEJ) pathway and is dependent on DNA-PKcs and XRCC4 (18-20). In addition to its role in the repair of strand breaks produced directly by genotoxic agents, hPNKP has been implicated in the repair of strand breaks produced by enzymatic processes, including strand breaks introduced by the βδ-AP lyase activity of DNA glycosylases such as NEIL1 and NEIL2 (21, 22), which generate 3'-phosphate termini. Similarly, hPNKP is required to process termini generated by the topoisomerase I inhibitor camptothecin (23). Treatment with camptothecin stalls topoisomerase I while it is covalently attached to a 3'-phosphate group in the course of its nicking-resealing activity. The stalled enzyme can be cleaved from the DNA by Tdp1 leaving a strand break with 3'-phosphate and 5'-hydroxyl termini, which necessitates the subsequent action of PNKP. Down-regulation of hPNKP by RNAi sensitized cells to a variety of genotoxic agents including ionizing radiation, camptothecin, methyl methanesulfonate and hydrogen peroxide (24). It remains to be determined which of hPNKP's activities, 5'-kinase or 3'-phosphatase (or both), is responsible for sensitization to each agent. The two activities are independent with separate DNA binding domains (25), but the phosphatase reaction appears to proceed ahead of the kinase reaction (26).

Synthetic lethality occurs when a combination of two protein knockouts is lethal, however the corresponding single mutations are viable. The original concept of synthetic lethality as it relates to DNA repair was discovered in 2005. The Ashworth and Helleday groups published two papers back to back in Nature, outlining synthetic lethality between BRCA−/− cells and inhibition of poly(ADP-ribose) polymerase (PARP).

It is, therefore, desirable to provide inhibitors of DNA repair proteins such as polynucleotide kinase/phosphatase and poly(ADP-ribose) polymerase, and their compounds, compositions, methods and kits and uses thereof.

This background information is provided for the purpose of making known information believed by the applicant to be of possible relevance to the present invention. No admission is necessarily intended, nor should it be construed, that any of the preceding information constitutes prior art against the present invention.

SUMMARY OF THE INVENTION

An object of the present invention is to provide a compound (s), composition(s), method(s) and/or kit for increasing the sensitivity of a cell(s) and/or tumour(s) to chemotherapeutic agents and/or ionizing radiation.

In accordance with one aspect of the present invention, there is provided, a compound or pharmaceutically acceptable salt thereof for increasing the sensitivity of a cancerous cell of a patient to a chemotherapeutic agent or radiation therapy, said compound comprising: 2-(1-hydroxyundecyl)-1-(4-nitrophenylamino)-6-phenyl-6,7a-dihydro-1H-pyrrolo[3,4-b]pyridine-5,7(2H,4aH)-dione (A12B4C3), 2-(hydroxy(phenyl)methyl)-1-(4-nitrophenylamino)-6-phenyl-6,7a-dihydro-1H-pyrrolo[3,4-b]pyridine-5,7(2H,4aH)-dione (A1B4C3), 2-(hydroxy(3,4,5-trimethoxyphenyl)methyl)-1-(4-nitrophenylamino)-6-phenyl-6,7a-dihydro-1H-pyrrolo[3,4-b]pyridine-5,7(2H,4aH)-dione (A6B4C3), tert-butyl 2-(1-hydroxy-2,2-diphenylethyl)-6-methyl-5,7-dioxo-2,4a,5,6,7,7a-hexahydro-1H-pyrrolo[3,4-b]pyridin-1-ylcarbamate (A26B11C2), or 2-(hydroxy(thiophen-2-yl)methyl)-6-methyl-1-(phenylamino)-6,7a-dihydro-1H-pyrrolo[3,4-b]pyridine-5,7(2H,4aH)-dione (A39B1C2).

In accordance with another aspect of the present invention, there is provided a method of chemosensitizing or radiosensitizing a cancerous cell in a mammal in need of chemotherapy or radiation therapy, comprising: administering to said mammal a compound or pharmaceutically acceptable salt thereof selected from A12B4C3, A1B4C3, A6B4C3, A26B11C2 or A39B1C2.

In accordance with another aspect of the present invention, there is provided a method of inhibiting the phosphatase activity of PNK, comprising: contacting a cell with a compound or pharmaceutically acceptable salt thereof selected from A12B4C3, A1B4C3, A6B4C3, A26B11C2 or A39B1C2.

In accordance with another aspect of the present invention, there is provided an improved method for radiation therapy of a patient with a neoplasm employing a radiation sensitizer, wherein the improvement comprises treating said patient with an effective amount of a compound or pharmaceutically acceptable salt thereof selected from A12B4C3, A1B4C3, A6B4C3, A26B11C2 or A39B1C2 as the radiation sensitizer.

In accordance with another aspect of the present invention, there is provided an improved method for chemotherapy therapy of a patient with a neoplasm employing a chemosensitizer, wherein the improvement comprises treating said patient with an effective amount of a compound or pharmaceutically acceptable salt thereof selected from A12B4C3, A1B4C3, A6B4C3, A26B11C2 or A39B1C2 as the chemosensitizer.

In another aspect of the present invention, there is provided a kit for increasing the sensitivity of a cancerous cell to a chemotherapeutic agent or radiation therapy said kit comprising: a compound or pharmaceutically acceptable salt thereof selected from A12B4C3, A1B4C3, A6B4C3, A26B11C2 or A39B1C; and instructions for the use thereof.

In another aspect of the present invention, there is provided a method of treating a subject suffering from a disorder associated with a defect in DNA polymerase β, comprising administering to said subject an inhibitor of PNKP.

In another aspect of the present invention, there is provided a pharmaceutical composition comprising: a first amount of a topoisomerase I inhibitor and a second amount of a PNKP inhibitor, and a pharmaceutically acceptable carrier.

In another aspect of the present invention, there is provided a combination comprising a topoisomerase I inhibitor and a PNKP inhibitor In accordance with another aspect of the present invention, there is provided a compound(s), composition(s), method(s) and/or kit for inhibiting PNKP phosphatase activity.

In accordance with another aspect of the present invention, there is provided a compound for increasing the sensitivity of a cell and/or tumour to a chemotherapeutic agent and/or ionizing radiation, the compound comprising:

2-(1-hydroxyundecyl)-1-(4-nitrophenylamino)-6-phenyl-6,7a-dihydro-1H-pyrrolo[3,4-b]pyridine-5,7(2H,4aH)-dione (A12B4C3), 2-(hydroxy(phenyl)methyl)-1-(4-nitrophenylamino)-6-phenyl-6,7a-dihydro-1H-pyrrolo[3,4-b]pyridine-5,7(2H,4aH)-dione (A1B4C3), 2-(hydroxy(3,4,5-trimethoxyphenyl)methyl)-1-(4-nitrophenylamino)-6-phenyl-6,7a-dihydro-1H-pyrrolo[3,4-b]pyridine-5,7(2H,4aH)-dione (A6B4C3), tert-butyl 2-(1-hydroxy-2,2-diphenylethyl)-6-methyl-5,7-dioxo-2,4a,5,6,7,7a-hexahydro-1H-pyrrolo[3,4-b]pyridin-1-ylcarbamate (A26B11C2), or 2-(hydroxy(thiophen-2-yl)methyl)-6-methyl-1-(phenylamino)-6,7a-dihydro-1H-pyrrolo[3,4-b]pyridine-5,7(2H,4aH)-dione (A39B1C2).

In accordance with one aspect of the present invention there is provided a chemosensitization and/or radiosensitization method to treat a cell in vitro and/or in vivo comprising administering to said cell a compound comprising A12B4C3, A1B4C3, A6B4C3, A26B11C2 or A39B1C2.

In a specific example the cell is A549 or MDA-MB-231.

In another aspect of the present invention, there is provided a method of radiosensitizing tumor cells in a mammal in need of radiation therapy, comprising administering to said mammal a compound selected from A12B4C3, A1B4C3, A6B4C3, A26B11C2 or A39B1C2

In one aspect of the present invention there is provided a use of a compound selected from A12B4C3, A1B4C3, A6B4C3, A26B11C2 or A39B1C2 in the preparation of a pharmaceutical composition for use as a radiosensitizer.

In one aspect of the present invention there is provided a use of a compound selected from A12B4C3, A1B4C3, A6B4C3, A26B11C2 or A39B1C2 in the preparation of a pharmaceutical composition for use as a chemosensitizer.

In one aspect of the present invention there is provided a use of a compound selected from A12B4C3, A1B4C3, A6B4C3, A26B11C2 or A39B1C2 in the preparation of a pharmaceutical composition for use as an inhibitor of the phosphatase activity of PNKP.

In a specific example, the phosphatase activity of PNKP is selected from human PNKP or mouse PNKP.

In accordance with another aspect of the present invention there is provided PNKP phosphatase inhibitor selected from A12B4C3, A1B4C3, A6B4C3, A26B11C2 or A39B1C2 to prepare a pharmaceutical composition to prevent or treat a cancer in a mammal, wherein the pharmaceutical composition is intended for administration in combination with a chemotherapeutic agent and/or ionizing radiation used in a treatment of a cancer.

In a specific example, the chemotherapeutic agent is a topoisomerase I inhibitor. In a specific example, the topoisomerase inhibitor is Camptothecin.

In another specific example, the ionizing radiation is γ-radiation. In one example, the ionizing radiation is X-rays generated by a linear accelerator (Linac).

In accordance with another aspect of the present invention, there is provided an improved method for radiation therapy of a patient with a neoplasm employing a radiation sensitizer, wherein the improvement comprises treating said patient with an effective amount of a compound selected from A12B4C3, A11B4C3, A6B4C3, A26B11C2 or A39B1C2 as the radiation sensitizer.

In accordance with another aspect of the present invention, there is provided an improved method for chemotherapy therapy of a patient with a neoplasm employing a chemosensitizer, wherein the improvement comprises treating said patient with an effective amount of a compound selected from A12B4C3, A1B4C3, A6B4C3, A26B11C2 or A39B1C2 as the chemosensitizer.

In accordance with one aspect of the present invention, there is provided method of treating a mammal diagnosed with cancer, said method comprising administering to said mammal a therapeutically effective amount of a pharmacological composition comprising a compound selected from A12B4C3, A1B4C3, A6B4C3, A26B11C2 or A39B1C wherein said composition contacts a cancer cell or tumour in said mammal, thereby making said cancer cell or tumour more susceptible to the effects of chemotherapy and/or ionizing radiation.

In a specific example, the chemotherapeutic agent is a topoisomerase I inhibitor. In a specific example, the topoisomerase inhibitor is Camptothecin.

In another specific example, the ionizing radiation is γ-radiation. In one example, the ionizing radiation is X-rays generated by a linear accelerator (Linac).

In accordance with another aspect of the present invention there is provided a kit for increasing the sensitivity of a cell(s) and/or tumour(s) to a chemotherapeutic agent and/or ionizing radiation or for inhibiting the phosphatase activity of PNKP, said kit comprising:
(i) a compound selected from A12B4C3, A1B4C3, A6B4C3, A26B11C2 or A39B1C; and
(ii) instructions for the use thereof.

In a specific example, the chemotherapeutic agent is a topoisomerase I inhibitor. In a specific example, the topoisomerase inhibitor is Camptothecin.

In another specific example, the ionizing radiation is γ-radiation. In one example, the ionizing radiation is X-rays generated by a linear accelerator (Linac).

In another specific example, the phosphatase activity PNKP is human PNKP, or mouse PNKP.

In accordance with another aspect of the present invention, there is provided a method for the treatment of a subject suffering from a disorder, such as cancer, associated with a defect in DNA polymerase β, comprising administering to said subject an inhibitor of PNKP. In one example the inhibitor of PNKP is A12B4C3 (also referred to as H5 herein, and in the Figures).

In accordance with another aspect of the present invention, there is provided a method for the treatment of a subject suffering from a disorder, such as cancer, associated with a defect in PNKP or DNA-PK, comprising administering to said subject an inhibitor of PARP In one example the inhibitor of PARP is DPQ.

BRIEF DESCRIPTION OF THE DRAWINGS

Embodiments of the present invention will now be described, by way of example only, with reference to the attached Figures, wherein:

FIG. 2 depicts the chemical structures and names of the compounds found to inhibit hPNKP phosphatase activity;

DETAILED DESCRIPTION

Figure 1:
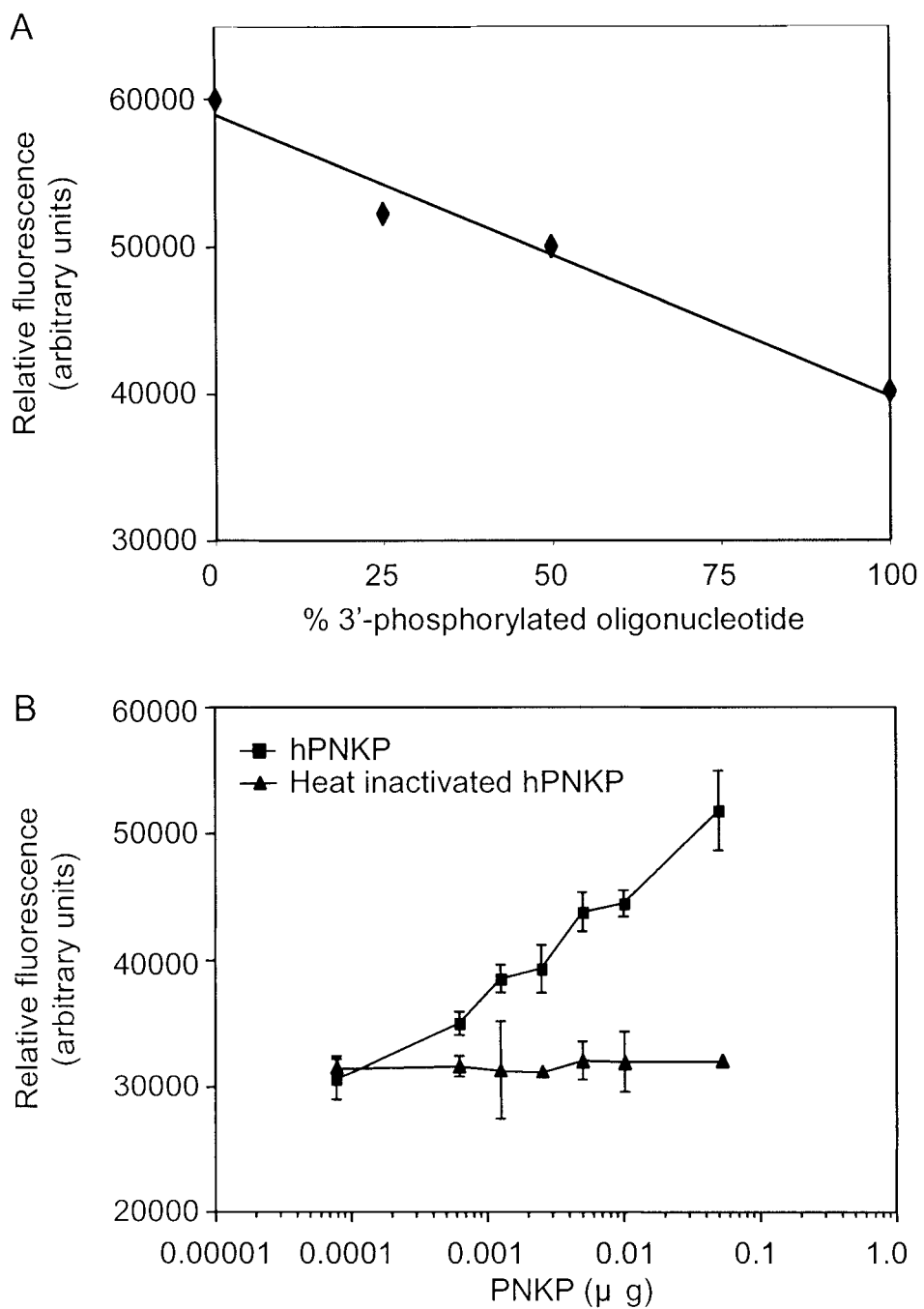
FIG. 1 (Panel A) depicts a typical phosphatase standard curve for the fluorescence quenching-based phosphatase assay. Readings were taken for solutions consisting of 0, 25, 50 and 100% phosphorylated oligos (r=0.99). A fresh standard curve was generated each time the screening assay was performed. (Panel B) depicts loss of fluorescence quenching resulting from increased removal of the 3'-phosphate group from the substrate with increasing quantity of hPNKP in the reaction. The data are combined from 3 independent determinations±S.E.M. (Panel C) depicts results of the screening assay for eight of the small molecules tested. Compounds A4B8C2, A28B3C1 and A24B12C3 failed to show any quenching of the sensor molecule as a result of hPNKP inhibition, while A12B4C3, A1B4C3, A6B4C3, A26B11C2 and A39B1C2 all displayed marked inhibition of substrate dephosphorylation. The data are combined from 3 independent determinations±S.E.M.

As will be described in more detail below, the present invention relates to compounds, compositions, methods and kits for increasing the sensitivity of cells and/or tumours to chemotherapeutic agents and/or ionizing radiation.

Also as will be discussed in more detail below, the present invention relates to inhibitors of polynucleotide kinase/phosphatase and poly(ADP-ribose) polymerase.

In one aspect of the present invention, the compound(s) and composition(s) of the present invention inhibit PNKP phosphatase activity. In specific examples of the present invention, the compound(s) and composition(s) of the present inhibit the DNA phosphatase activity of human PNKP or mouse PNKP.

As used herein, the term "inhibit" with respect to phosphatase activity is intended to include partial or complete inhibition of phosphatase activity.

In accordance with one aspect of the present invention, there is provided radiosensitizer and chemosensitizer compounds and compositions, methods and kits and the uses thereof.

The term "radiosensitizer", as used herein refers to an agent, molecule, compound or composition that enhances the sensitivity of a neoplastic cell, a cancer cell and/or a tumor to the effects of radiation. The "sensitivity" of a neoplastic cell, a cancer cell, and/or a tumour to radiation is the susceptibility of the neoplastic cell, cancer cell, and/or tumour to the inhibitory effects of radiation on the cell's or tumour's growth and/or viability The term "chemosensitizer", as used herein, refers to an agent, molecule, compound or composition that enhances the sensitivity of a neoplastic cell, a cancer cell and/or a tumor to the effects of a chemotherapeutic agent. The "sensitivity" of a neoplastic cell, a cancer cell, and/or a tumour to a chemotherapeutic agent is the susceptibility of the neoplastic cell, cancer cell, and/or tumour to the inhibitory effects of a chemotherapeutic agent on the cell's or tumour's growth and/or viability.

Compound(s)/Composition(s)

In one aspect of the present invention, the compound(s) of the present invention increase radiosensitivity and/or chemosensitivity of a cell(s) and/or tumour(s).

In another aspect of the present invention, the compound(s) of the present invention reduce cell survival of cells depleted with DNA polymerase β or PARP.

In another aspect of the present invention, the compound(s) of the present invention inhibits the phosphatase activity of PNKP.

The compounds of the present invention are capable of forming a variety of different salts with various inorganic and organic acids. Such salts are pharmaceutically acceptable for administration to a subject.

In a specific example, the compound(s) and composition(s) of the present invention increase sensitivity of a cell and/or tumour to radiation.

About half of patients with cancer are treated with radiation therapy, either alone or in combination with other types of cancer treatment. Radiation therapy (also referred to as radiotherapy, X-ray therapy, or irradiation) may be external, internal and systemic.

External radiation is delivered from a machine outside the body; internal radiation is implanted into or near the tumour (s); systemic radiation utilizes unsealed radiation sources.

External radiation therapy is used to treat most types of cancer, including but not limited to, cancer of the bladder, brain, breast, cervix, larynx, lung, prostate, and vagina. Intraoperative radiation therapy (IORT) is a form of external radiation that is given during surgery, and can be used to treat localized cancers that cannot be completely removed or that have a high risk of recurring in nearby tissues, including, but not limited to treatment of thyroid and colorectal cancers, gynecological cancers, cancer of the small intestine, and cancer of the pancreas. Prophylactic cranial irradiation (PCI) is another type of external radiation given to the brain when the primary cancer (for example, small cell lung cancer) has a high risk of spreading to the brain.

Internal radiation therapy (or brachytherapy) typically uses radiation source sealed in a small holder called an implant. Implants may be in the form of thin wires, plastic tubes called catheters, ribbons, capsules, or seeds. Interstitial radiation therapy, a type of internal radiation therapy) is inserted into tissue at or near the tumour site. It is used to treat tumors of the head and neck, prostate, cervix, ovary, breast, and perianal and pelvic regions. Intracavitary or intraluminal radiation therapy is inserted into the body with an applicator. It is commonly used in the treatment of uterine cancer, and may have application in other cancers, including breast, bronchial, cervical, gallbladder, oral, rectal, tracheal, uterine, and vaginal.

Systemic radiation therapy uses materials such as iodine 131 and strontium 89, and may be taken by mouth or injected. Such therapy may be used in the treatment of cancers of the thyroid and adult non-Hodgkin lymphoma.

In a specific example, the radiation is γ-radiation. In one example, the ionizing radiation is X-rays generated by a linear accelerator (Linac In another example, the compound(s) and composition(s) of the present invention increases sensitivity of a cell(s) and/ or tumour(s) to a chemotherapeutic agent. In one example, the chemotherapeutic agent is a topoisomerase I inhibitor.

The term "topoisomerase I inhibitor" as used herein includes, but is not limited to topotecan (HYCAMTIN®), gimatecan, irinotecan (CAMPTOSAR®), camptothecin and its analogues.

Indications, routes and methods of administration, and the like, of topoisomerase I inhibitors are known to the skilled worker.

CAMPTOSAR® injection, for example, is indicated as a component of first-line therapy in combination with 5-fluorouracil and leucovorin for patients with metastatic carcinoma of the colon or rectum. CAMPTOSAR is also indicated for patients with metastatic carcinoma of the colon or rectum whose disease has recurred or progressed following initial fluorouracil-based therapy.

HYCAMTIN for Injection, for example, is indicated for: metastatic carcinoma of the ovary after failure of initial or subsequent chemotherapy, small cell lung cancer sensitive disease after failure of first-line chemotherapy, combination therapy with cisplatin for stage IV-B, recurrent, or persistent carcinoma of the cervix which is not amenable to curative treatment with surgery and/or radiation therapy.

HYCAMTIN capsules, for example, is indicated for treatment of patients with relapsed small cell lung cancer In a specific example, the topoisomerase I inhibitor is camptothecin.

In accordance with a specific example of the present invention, the compound(s) of the present invention increases sensitivity to ionizing radiation and/or chemotherapy, the compound(s) comprising:

2-(1-hydroxyundecyl)-1-(4-nitrophenylamino)-6-phenyl-6,7a-dihydro-1H-pyrrolo[3,4-b]pyridine-5,7(2H,4aH)-dione (A12B4C3), 2-(hydroxy(phenyl)methyl)-1-(4-nitrophenylamino)-6-phenyl-6,7a-dihydro-1H-pyrrolo[3,4-b]pyridine-5,7(2H,4aH)-dione (A1B4C3), 2-(hydroxy(3,4,5-trimethoxyphenyl)methyl)-1-(4-nitrophenylamino)-6-phenyl-6,7a-dihydro-1H-pyrrolo[3,4-b]pyridine-5,7(2H,4aH)-dione (A6B4C3), tert-butyl 2-(1-hydroxy-2,2-diphenylethyl)-6-methyl-5,7-dioxo-2,4a,5,6,7,7a-hexahydro-1H-pyrrolo[3,4-b]pyridin-1-ylcarbamate (A26B11C2), or 2-(hydroxy(thiophen-2-yl)methyl)-6-methyl-1-(phenylamino)-6,7a-dihydro-1H-pyrrolo[3,4-b]pyridine-5,7(2H,4aH)-dione (A39B1C2).

In another aspect of the present invention, there are provided pharmaceutical compositions and methods of treatment using such pharmaceutical compositions for therapeutic uses.

In one example of the present invention, there is provided pharmaceutical compositions comprising A12B4C3, A1B4C3, A6B4C3, A26B11C2 or A39B1C2 together with pharmaceutically acceptable diluents or carriers.

Suitable pharmaceutical carriers include inert diluents or fillers, water and various organic solvents.

The pharmaceutical composition may, if desired, contain additional ingredients such as flavorings, binders, excipients and the like.

The compounds of the present invention are synthesized as has been described before (12), the entire contents of this disclosure are incorporated herein by reference.

In another aspect of the present application, inhibitors of PNKP are used to reduce survival of cells depleted in DNA polymerase β. In one example, the inhibitor of PNKP is A12B4C3 (also referred to as H5 herein, and in the Figures). In this example, A12B4C3 (also referred to as H5 herein, and in the Figures) reduced survival of DNA Polymerase β Dominant Negative (Pol β DN) cells.

Accordingly, there is provided a potential synthetic lethal therapeutic strategy for the treatment of cancers with specific DNA-repair defects, including those arising in carriers of a DNA Polymeraseβ mutation.]

In another aspect of the present application, inhibitors of PARP are used to reduce survival of cells depleted in PNKP or DNA-PK. In one example, the inhibitor of PARP is 3,4-dihydro-5[4-(1-piperindinyl)butoxy]-1(2H)-isoquinoline (DPQ).

In one example, DPQ reduced survival of A549δPNKP (polynucleotide kinase/phosphatase (PNKP) depleted) cells. In one example, DPQ reduced survival of M059J (non-functional DNA-dependent protein kinase (DNA-PK)) cells.

PARP inhibitors may be useful in the treatment of pancreatic cancer, solid tumours, melanoma, colorectal cancer, breast cancer, ovarian cancer, non-small cell lung cell cancer, sarcoma, glioblastoma multiforme.

Additional examples of PARP inhibitors include, but are not limited to, BSI401 (BiPar Science Inc.); CPH101 with CPH102 (Crimson Pharma); GPI21016 (Eisai Co.); ABT888 and ABT888 with Temozolomide (Abbott Laboratories); AZD2281 and AZD2281 with Avastin, Caelyx, Carboplatin, Carboplatin/paclitaxel, Dacadbazine, gemcitabine or paclitaxel (AstraZeneca Plc); MK4827 (Merk & Co. Inc); AZD2281 and AZD2281 with cisplatin or paclitaxel (AstraZeneca Plc); BSI201 and BSI201 with carboplatin/paclitaxel, chemotherapy, irinotecan, temodar and radiation; or topotecan (BiPar Science Inc); AG014699 or AG14699 with temozolomide (Pfizer Inc); BSI201 with gencitabine and carboplatin; PARP 1 Sentineal (Sentinel oncology).

The following Table depicts examples non-limiting example PARP inhibitors, the phase of testing and indication(s).

| Company | Product | Phase | Indication |
|---|---|---|---|
| BiPar Sciences, Inc. | BSI401 | PC | Pancreatic Cancer |
| Crimson Pharma | CPH101 with CPH102 | PC | Cancer |
| Eisai Co. | GPI21016 | PC | Cancer (Cancer Chemosensitization and Radiosensitization) |
| Abbott Laboratories | ABT888 | I | Cancer |
|  | ABT888 with Temozolomide | I | Solid Tumors |
| AstraZeneca Plc | AZD2281 with Avastin | I | Solid Tumors (Advanced Solid Tumors) |
|  | AZD2281 with Caelyx | I | Solid Tumors (Advanced Solid Tumors) |
|  | AZD2281 with Carboplatin | I | Solid Tumors (Advanced Solid Tumors) |
|  | AZD2281 with Carboplatin, Paclitaxel | I | Solid Tumors (Advanced Solid Tumors) |
|  | AZD2281 with Dacarbazine | I | Melanoma (Advanced Melanoma) |
|  | AZD2281 with Gemcitabine | I | Pancreatic Cancer |
|  | AZD2281 with Paclitaxel | I | Solid Tumors (Advanced Solid Tumors) |

-continued

| Company | Product | Phase | Indication |
|---|---|---|---|
| BiPar Sciences, Inc. | BSI201 | I | Solid Tumors (Solid Tumors (Monotherapy)) |
| | BSI201 | I | Solid Tumors |
| Cephalon Inc | CEP9722 | I | Solid Tumors |
| Merck & Co Inc | MK4827 | I | Solid Tumors (Ovarian Neoplasm) |
| AstraZeneca Plc | AZD2281 | II | Colorectal Cancer |
| | AZD2281 | II | Breast Cancer (Advanced Breast Cancer) |
| | AZD2281 | II | Ovarian Cancer (BRCA Deficient Advanced Ovarian Cancer) |
| | AZD2281 with Cisplatin | II | Breast Cancer (Triple Negative Breast Cancer) |
| | AZD2281 with Paclitaxel | II | Breast Cancer (Metastatic Triple Negative Breast Cancer) |
| BiPar Sciences, Inc. | BSI201 | II | Pancreatic Cancer (BRCA-Negative Pancreatic Cancer) |
| | BSI201 | II | Ovarian Cancer (BRCA-Negative Ovarian Cancer (Monotherapy)) |
| | BSI201 with Carboplatin, Paclitaxel | II | Cancer (Uterine Carcinosarcoma) |
| | BSI201 with Carboplatin, Paclitaxel | II | Non-Small-Cell Lung Cancer |
| | BSI201 with Chemotherapy | II | Sarcoma |
| | BSI201 with Irinotecan | II | Breast Cancer (Metastatic Breast Cancer) |
| | BSI201 with Temodar and Radiation Therapy | II | Brain Tumor (Newly Diagnosed Glioblastoma Multiforme) |
| | BSI201 with Topotecan | II | Ovarian Cancer (Advanced Ovarian Cancer) |
| Pfizer Inc (PFE) | AG014699 | II | Breast Cancer |
| | AG14699 | II | Cancer |
| | AG14699 | II | Ovarian Cancer |
| | AG14699 with Temozolomide | II | Melanoma (Metastatic Malignant Melanoma) |
| BiPar Sciences, Inc. (Private) | BSI201 with Gemcitabine and Carboplatin | III | Breast Cancer (Metastatic Triple Negative Breast Cancer) |
| LEAD Therapeutics, Inc. (Private) | PARP Inhibitor Program LEAD THERAPEUTICS | NA | Cancer |
| Sentinel Oncology | PARP 1 SENTINEL | NA | Solid Tumors (Tumors) |

Thus, in one aspect of the present invention there is provided a potential synthetic lethal therapeutic strategy for the treatment of cancers with specific DNA-repair defects, including those arising in carriers of a PNKP or DNA-PK mutation.

Compounds of the present invention may be administered with a physiologically acceptable carrier. A physiologically acceptable carrier is a formulation to which the compound can be added to dissolve it or otherwise facilitate its administration. Non limiting examples include, but are not limited to, water, saline, physiologically buffered saline.

Solid dosage forms for oral administration can include capsules, tablets, pills, powders, and granules. In such forms, the compounds of the present invention may be combined with one or more adjuvants, as indicated by the route of administration. Compounds of the present invention can be admixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

Compounds and pharmaceutically acceptable compositions of the present invention can be administered by parenteral administration, in the form of aqueous or non-aqueous isotonic sterile injection solutions or suspensions. These solutions and suspensions can be prepared from sterile powders or granules having one or more of the carriers or diluents mentioned for use in the formulations for oral administration. Compounds of the present invention can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art, as know by the skilled worker.

Liquid dosage forms for oral administration include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

It will be appreciated that the amount of active ingredient that can be combined with the carrier materials to produce a single dosage form varies depending upon the mammalian host treated and the particular mode of administration.

The compounds and compositions of the present invention are suitable for combination. Combination therapy as used herein includes administration of the therapeutic agents in a sequential manner, wherein each therapeutic agent is administered at a different time, as well as administration of the therapeutic agents at the same time.

As used herein, the therapeutic agents are administered in a sequential manner, wherein each therapeutic agent is administered at a different time, or administered in a generally simultaneous manner. The generally simultaneous administration can be accomplished, for example, by administering to the subject a single capsule having a fixed ratio of each therapeutic agent or in multiple, single capsules for each of the therapeutic agents.

Administration of each therapeutic agent, whether sequential or generally simultaneous, can be effected by any appropriate route including, but not limited to, oral routes, intravenous routes, intramuscular routes, and direct absorption through mucous membrane tissues, etc. The therapeutic agents can be administered by the same route or by different routes.

Combination therapy also includes administration of the therapeutic agents in combination with other biologically active ingredients (such as, but not limited to, a second and different antineoplastic agent) and non-drug therapies (such as, but not limited to, surgery or radiation therapy).

Where the combination therapy further comprises radiation therapy, the radiation therapy may be conducted at a suitable time so long as a beneficial effect from the co-action of the combination of the therapeutic agents and radiation treatment is achieved.

Method(s)

In accordance with another aspect of the present invention, there is provided a method(s) for increasing the sensitivity of a cell(s) and/or tumour(s) to chemotherapeutic agents and/or ionizing radiation.

In accordance with another aspect of the present invention, there is provided a method(s) for inhibiting PNKP phosphatase activity. In one aspect of the present invention, the PNKP is human PNKP. In one aspect of the present invention, the PNKP is mouse PNKP. In another example, the PNKP is a mammalian PNKP.

In one aspect of the present invention, increasing the sensitivity of a cell(s) and/or tumour(s) to chemotherapeutic agents and/or ionizing radiation is carried out in vitro, including, but not limited to, in cultured cells. In a specific example, the cultured cells are A549 and/or MDA-MB-231 cells.

In one aspect of the present invention, inhibition of the phosphatase activity of PNKP is carried out in vitro, including, but not limited to, in cultured cells. In a specific example, the cultured cells are A549 and/or MDA-MB-231 cells.

In another aspect of the present invention, increasing the sensitivity of a cell(s) and/or tumour(s) to chemotherapeutic agents and/or ionizing radiation, and inhibiting the phosphatase activity of PNKP, is carried out in vivo in a subject The term "subject", as used herein, refers to any human or animal whom would benefit from treatment with a chemosensitizer and/or a radiosensitizer, and/or has a disorder associated with PNKP. Non-limiting examples of a subject include humans, non-human mammal, rodents, companion animals, livestock and the like.

The compound(s) and composition(s) according to the present invention are chemosensitizers and/or radiosensitizers useful for the treatment of cancer. In one aspect of the present invention, the methods, compound(s) and composition(s) of the present invention may be used for the treatment of neoplasia disorders including benign, metastatic and malignant neoplasias.

Another embodiment of the present invention relates to treating or lessening the severity of one or more diseases in which PNKP is known to play a role. In one example, the disease is cancer.

By the terms "treating" or "lessening the severity", it is to be understood that any reduction using the methods, compounds and composition disclosed herein, is to be considered encompassed by the invention. Treating or lessening in severity, may, in one embodiment comprise enhancement of survival, or in another embodiment, halting disease progression, or in another embodiment, delay in disease progression, or in another embodiment, diminishment of pain, or in another embodiment, delay in disease spread to alternate sites, organs or systems. Treating or lessening in severity, may, in one embodiment, comprise a reduction in the amount/dosage of radiotherapy and/or chemotherapy otherwise required to treat a subject, thereby resulting in a reduction of normal tissue damage. It is to be understood that any clinically beneficial effect that arises from the methods, compounds and compositions disclosed herein, is to be considered to be encompassed by the invention.

The term "pharmaceutically effective amount" as used herein refers to the amount of a drug or pharmaceutical agent that will elicit the biological or medical response of a tissue, system, animal or human that is being sought by a researcher or clinician. This amount can be a therapeutically effective amount.

In accordance with another aspect of the present invention, there is provided a method(s) for the treatment of a subject, including a human, suffering from a cancer comprising administering to said subject a compound comprising A12B4C3, A1B4C3, A6B4C3, A26B11C2 or A39B1C2, a pharmaceutically acceptable salt, in combination with chemotherapy and/or radiotherapy.

In accordance with another aspect of the present invention, there is provided a method for the treatment of a subject suffering from a disorder, such as cancer, associated with a defect in DNA polymerase β, comprising administering to said subject an inhibitor of PNKP. In one example the inhibitor of PHNP is A12B4C3 (also referred to as H5 herein, and in the Figures).

Studies have suggested that ~30% of human tumours express DNA Polymerase β variants (see Starcevic D et al. (2004) Cell Cycle 3: 998-1001). The highest proportions of variants are in gastric, colorectal and esophageal cancers, and also been found in lung, breast, prostate and bladder cancers.

In accordance with another aspect of the present invention, there is provided a method for the treatment of a subject suffering from a disorder, such as cancer, associated with a defect in PNKP or DNA-PK, comprising administering to said subject an inhibitor of PARP. In one example the inhibitor of PARP is DPQ.

As used herein, the term "pharmaceutically acceptable salt" refers to those salts which are, within the scope of sound medical judgment, suitable for use in contact with the cell(s) and/or tissue(s) of a subject without undue toxicity, irritation, allergic response and the like, and are commensurate with a reasonable benefit/risk ratio.

Methods of the present invention are conveniently practiced by providing the compound(s) and/or composition(s) used in such method in the form of a kit. Such a kit preferably contains the instructions of the use thereof.

To gain a better understanding of the invention described herein, the following examples are set forth. It should be understood that these example are for illustrative purposes only. Therefore, they should not limit the scope of this invention in any way.

EXAMPLE-I

Materials and Methods

Enzymes

Recombinant human PNKP was purified as described previously (14, 29) and stored in 50 mM Tris-HCl, pH 7.4, 100 mM NaCl, 5 mM MgCl$_2$, 0.5 mM dithiothreitol. Recombinant mouse PNKP was purified as previously described (25). *Schizosaccharomyces pombe* PNKP was purified as described previously (30). Phage T4 polynucleotide kinase (T4 PNK) was purchased from Roche Diagnostics (Indianapolis, Ind.). Human PP-1cγ protein was expressed in *E. coli* and purified as previously described (31). Rat δ-calcineurin protein was expressed in *E. coli* and purified as previously described (32).

Human recombinant aprataxin (APTX) protein with an N-terminal 6× His tag was expressed in BL21-Gold (DE3) *E. coli* competent cells (Stratagene, La Jolla, Calif.) using the QIAgene expression construct (Qiagen, Mississauga, ON). A single colony of kanamycin resistant *E. coli* was used to inoculate a 200-ml overnight culture (e.g, about 12 to about 16 hours in Luria-Bertani (LB) media containing 30 µg/ml kanamycin. Four 50-ml fractions of overnight culture were then subcultured into 4×1 L LB without kanamycin. Once the culture reached an optical density of ~0.6 at 600 nm, protein expression was induced using 0.2 mM isopropyl-1-thio-β-galactopyranoside (Sigma, St Louis, Mo.) at 37° C. for 2 hours. Cells were harvested by centrifugation at 10,000 rpm for 10 minutes at 4° C. and resuspended in 40 ml buffer (50 mM $NaH_2PO_4$, 250 mM NaCl, 1 mM PMSF, at pH 7.9). The solution was then stirred on ice for 30 minutes in the presence of 30 mg lysozyme and 4 mg PMSF, 1 µg/ml each of pepstatin and leupeptin. The bacteria were then sonicated 6×30 seconds allowing 30 seconds between intervals to cool down. The cell debris was then spun down at 15,000 rpm for 15 minutes at 4° C. and the supernatant collected. The supernatant was then stirred on ice in the presence of 4 ml Probond resin (Invitrogen, Burlinton, ON) for 1 hour and then loaded onto a column. The resin was washed with 3×5 ml 20 mM imidazole and 5 ml fractions were collected. Then, 25 ml of 150 mM imidazole was loaded onto the column and 1 ml fractions were collected. Fractions were run on a 10% SDS-PAGE and stained with Coomassie Brilliant Blue R-250 (Invitrogen). Fractions showing high concentrations and single bands were then combined and concentrated using a 30 kDa cutoff Amicon Ultra-15 centrifugal filter (Millipore, Etibicoke, ON) and dialyzed with 50 mM Tris-HCl (pH 7.5), 100 mM NaCl, and 5 mM $MgCl_2$. His-APTX concentration was then determined using the Bio-Rad Protein assay (Bio-Rad, Mississauga, ON).

Cells

A549 (human lung carcinoma cells) and MDA-MB-231 (human breast adenocarcinoma cells) were obtained from the American Type Culture Collection (Manassas, Va.). Cells were cultured in a 1:1 mixture of Dulbecco's modified Eagle's medium/nutrient mixture F-12 (DMEM/F-12) supplemented with 10% fetal calf serum (FCS), penicillin (50 U/ml), streptomycin (50 µg/ml), L-glutamine (2 mM), non-essential amino acids (0.1 mM) and sodium pyruvate (1 mM), and maintained at 37° C. under 5% $CO_2$ in a humidified incubator. All culture supplies were purchased from Invitrogen. The generation of PNKP-depleted A549 cells, termed "A549SPNKP" (also referred to as C-ter3), has been previously described (24). The PNKP-depleted MDA-MB-231, termed "MDA-MB-231δPNKP", cells were generated in a similar fashion except that the shRNA-expressing pSUPER vector used on this occasion (pSUPER.neo, OligoEngine, Seattle, Wash.) also contained the cDNA for the G418 selectable marker.

Optimization of Fluorescence Quenching-Based Assay for PNKP 3'-Phosphatase Activity.

The Lightspeed™ assay developed originally for protein kinases by QTL Biosystems (Santa Fe, N. Mex.) was modified. The standard substrate used for this assay was a 20-mer oligonucleotide (5'-TAMRA-AAT ACG AAT GCC CAC ACC GC-P-3') labelled with 5'-(6-carboxytetramethyl-rhodamine) at the 5'-end and bearing a terminal 3'-phosphate (Integrated DNA Technologies, Coralville, Iowa). The TAMRA-labelled oligonucleotide lacking a 3'-phosphate served as a control. Four standard solutions, consisting of 0, 25, 50 and 100% 3'-phosphorylated oligonucleotide, were prepared by mixing the two oligonucleotides in respective proportions (2.5 nM total oligonucleotide concentration). The assay was performed in 384-well white Optiplate microplates (PerkinElmer, Woodbridge, ON) in 70 mM Tris-HCl, pH 7.4, 60 mM $MgCl_2$, 5 mM $MnCl_2$, 0.3% BSA, 0.09% sodium azide. Reaction buffer was prepared by adding 1 mM DTT immediately prior to use. Five µL of 3'-phosphatase substrate (final concentration 0.5 µM) was used per well. In duplicate, 10 µl of each concentration of hPNKP was added per well. Plates were incubated for 1 hour at 37° C. and then 15 µl of 1× sensor solution (provided by QTL) was added to each well and incubated for 30 minutes at room temperature. Fluorescence (485 nm excitation and 520 nm emission wavelengths) of each well was read in a FLUOstar Optima® (BMG Labtech Inc, Durham, N.C.). Data were analyzed using GraphPad Prism® Software (San Diego, Calif.).

Screening the Small Molecule Library

A library of 244 small molecules (28) was used for the screening. Small molecules were provided in powder form and were dissolved in 100% DMSO and a final concentration of 100 µM was added to each well and assays were performed as described above.

After obtaining an optimum calibration curve and enzyme concentration curve, a simplified form of the assay to test the library in a short time, was employed. One concentration of hPNKP, 50 ng, was tested and compared with the control well with no enzyme. The assay was conducted in the same way as described above with respect to oligonucleotides, buffer, controls, incubation lengths/temperatures, centrifugations and sensor addition.

Assay for 3'-Phosphatase Activity Based on the Release of Inorganic Phosphate (Pi).

hPNKP phosphatase reactions (20 µl total volume) were set up as follows: 1 µl hPNKP (100 ng), 2 µl 10× phosphatase buffer (500 mM Tris-HCl, pH 7.4, 0.1 mM EDTA, 1 mM spermidine and 2.5 mM DTT), 2 µl of 1 mM 3'-P 20 mer oligonucleotide, 15 µl distilled $H_2O$ and 1 µl small molecule (varying concentrations). (The oligonucleotide had the same sequence as that used in the fluorescence quenching assay, but without the TAMRA substituent). The reactions were then transferred to a clear polystyrene colorimetric 384-well plate and incubated at 37° C. for 30 minutes. PiColorlock Gold reagent (Innova Biosciences Ltd., Cambridge, UK) was prepared shortly before use by addition of 1/100 vol. of accelerator to PiColorlock Gold reagent as directed by the manufacturer. The Gold mix was then added to Pi-containing samples in a volume ratio of 1:4 and the samples were then incubated at room temperature for 30 minutes before the absorbance was read at 620 nm using a FLUOstar Optima® plate reader (BMG Labtech Inc. Durham, N.C.)

Conventional Radio-Gel Assay for hPNKP 3'-Phosphatase Activity hPNKP phosphatase activity was determined by monitoring the removal of the 3'-phosphate from a 5'-$^{32}$P-labeled 20 mer oligonucleotide containing a 3'-phosphate (5'-ATT ACG AAT GCC CAC ACC GC-P-3') as previously described (14). Briefly, 5'-end of the oligomer was labelled by incubation with phage T4 phosphatase-free polynucleotide kinase (Roche Diagnostics, Indianapolis, IND.) and [γ-$^{32}$P]ATP (PerkinElmer). The labelled oligomer was then incubated with hPNKP for 20 minutes and the level of 3'-dephosphorylation was monitored by electrophoresis on a 12% polyacrylamide/7 M urea sequencing gel for 3 hours in 1×TBE buffer. Gels were scanned with a Typhoon 9400 Variable Mode Imager (GE Healthcare, Little Chalfont, UK), and quantified using Image Quant 5.2 Software (GE Healthcare).

PP-1cγ and Calcineurin Phosphatase Assay

PP-1cγ and calcineurin activity was analyzed, using a colorimetric p-nitrophenol phosphate (pNPP) assay as previously described (33). The reaction were carried out in a 96-well microplate with a final volume of 60 µl containing 40 µl of pNPP assay buffer (50 mM Tris, pH 7.4, 0.1 mM EDTA, 30 mM $MgCl_2$, 0.5 mM $MnCl_2$, 1 mg/ml BSA, 0.2% β-mercaptoethanol), 0.03 µg PP-1cγ (specific activity >30 units per mg) or a catalytically equivalent quantity of calcineurin and 10 µl of 0.5 mM DNA 3'-phosphatase inhibitor sample in DMSO or 10 µl of 50 µM A12B4C3 sample in DMSO, or control solvent. After a 10-minute incubation at 37° C., 10 µl of 30 mM pNPP was added to each well and incubated for an additional of 60 minutes and 45 minutes for PP-1cγ and calcineurin, respectively. The absorbance at 405 nm was measured using a SOFTmax 2.35 microplate reader (Molecular Devices, Sunnyvale, Calif.).

DNA Kinase Assay

Reaction mixtures (20 µl) containing kinase buffer (80 mM succinic acid (pH 5.5), 10 mM $MgCl_2$, and 1 mM DTT), 100 µM 20-mer oligonucleotide substrate, 3.3 pmol of [γ-32P] ATP, A12B4C3 (0-50 µM) in 2 µl DMSO, and 1 µg of PNK were incubated at 37° C. for 20 minutes. The reaction was stopped by addition of an equal volume of DNA loading dye (90% formamide, 0.02% bromophenol blue, 0.02% xylene cyanol in 1×TBE). Samples were boiled for 5 minutes and the products separated on a 12% polyacrylamide/8 M urea gel. Gels were scanned with a Typhoon 9400 Variable Mode Imager (GE Healthcare), and quantified using Image Quant 5.2 Software (GE Healthcare).

Cell Proliferation Assay

To determine the effect of the inhibition of PNKP by small molecule inhibitors on cell proliferation we used the CellTiter 96™ AQueous Non-Radioactive Cell Proliferation Assay (Promega, Madison Wis.), better known as the MTS assay. Approximately $2.5 \times 10^3$ A549 cells were plated in triplicate in a 96-well plate with different concentration of A12B4C3. After 72 hours, 20 µl of CellTiter 96 Aqueous One Solution Reagent was added to each well and cells were incubated for 4 more hours at 37° C. The absorbance recorded at 490 nm was used as the number of living cells in culture (FLUOstar Optima, BMG Labtechnologies).

Cytotoxicity Studies

The effect of hPNKP inhibition by A12B4C3 on cellular survival following exposure to ionizing radiation was measured in A549, A549γPNKP and MDA-MB-231 and MDA-MB-2318PNKP cells by clonogenic assays. Cells were seeded on 60-mm tissue culture plates at various concentrations to give between about 100-1000 colonies per plate and returned to the incubator overnight to allow the cells to attach. For radiosensitization studies, the cells were incubated with or without 1 µM A12B4C3 for 2 hours before irradiation and then exposed to increasing doses of γ-radiation ($^{60}$Co Gammacell; Atomic Energy of Canada Limited, Ottawa). After irradiation, cells were incubated for a further 24 hours in the same media and then washed twice with phosphate-buffered saline (PBS) and incubated in fresh media without the inhibitor. Colonies were stained with crystal violet after 10 to 14 days and counted with an automated Colcount colony counter (Oxford Optronix, Oxford, UK).

The effect of hPNKP inhibition by A12B4C3 on cellular survival following exposure to the topoisomerase I poison, camptothecin, was measured in A549 and A549δPNKP cells by the clonogenic survival assay (colony forming assay). Cells were seeded on 60-mm tissue culture plates at various concentrations to give between about 100-1000 colonies per plate and returned to the incubator overnight to allow the cells to attach. For chemosensitization studies, the cells were incubated with or without 1 mM A12B4C3 for 2 hours before addition of camptothecin and then exposed to increasing doses of camptothecin (Sigma). After addition of the topoisomerase I poison, cells were incubated for a further 24 hours in the same media and then washed twice with phosphate-buffered saline (PBS) and incubated in fresh media without the inhibitor. Colonies were stained with crystal violet after 10 to 14 days and counted with an automated Colcount colony counter (Oxford Optronix, Oxford, UK).

Results

Screening of the Library by a Fluorescence-Based Assay

The fluorescence-based phosphatase assay adapted was originally developed to monitor protein phosphatase activity (34). This assay involves a fluorescent sensor molecule coated in trivalent metal cations which causes superquenching of the sensor signal when in close proximity to a dye (TAMRA) on the substrate. The sensor is brought close to TAMRA via the ionic bond formed between the terminal DNA phosphate and the trivalent metal cations on the sensor. Removal of the phosphate leads to an elevation of fluorescence because the sensor is not brought close enough to TAMRA for its signal to be quenched. The buffer conditions were modified so that the internucleotide phosphate groups of a DNA substrate would not interfere strongly with the process of measuring the presence of a terminal phosphate group as shown by the standard curve of 0, 25, 50 and 100% phosphorylated oligo solutions (FIG. 1A). The amount of hPNKP required for near complete dephosphorylation of the oligonucleotide was determined by measuring the fluorescence signal as a function of hPNKP present in the reaction (FIG. 1B), and as a result 50 ng was chosen as the standard quantity of hPNKP for each reaction in the screen. Heat inactivated hPNKP was used as a control.

Figure 1C:
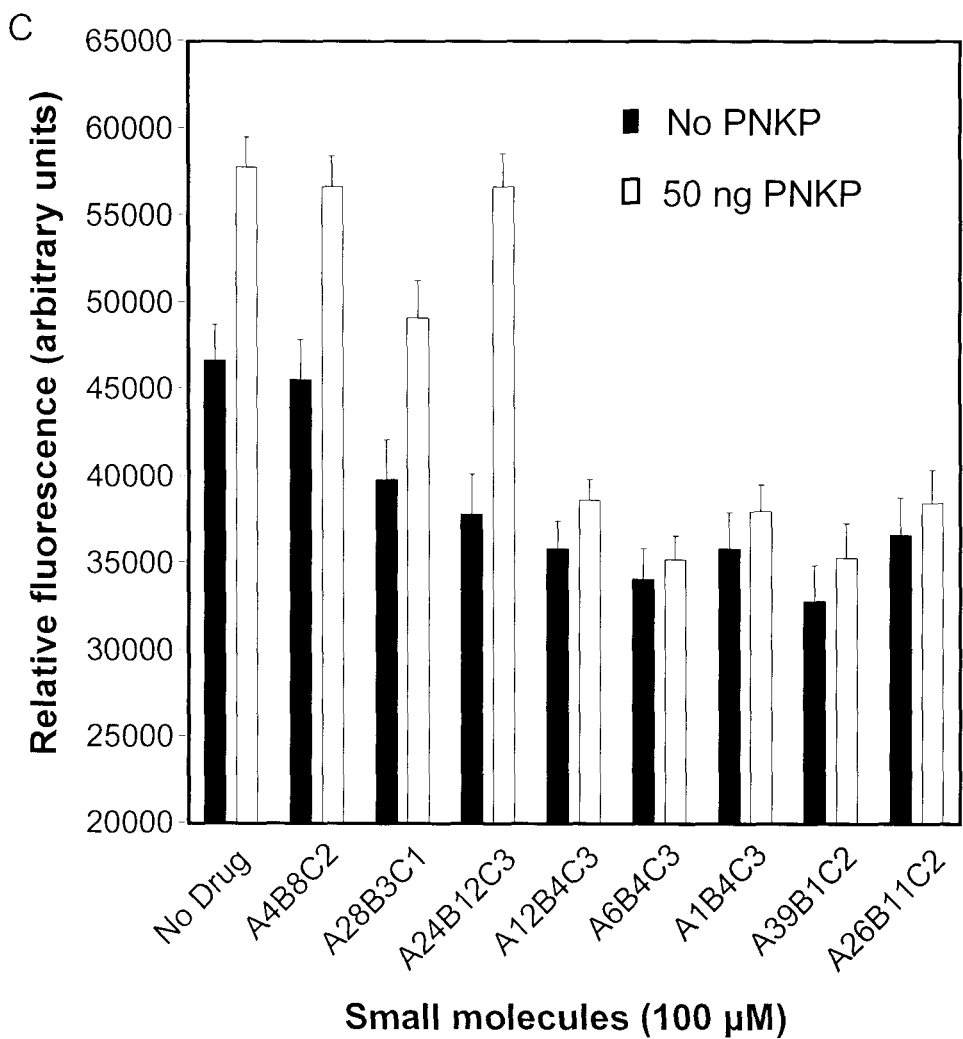

A chemical library containing over 200 polysubstituted piperidene molecules (28) was screened for their capacity to inhibit the phosphatase activity of human PNKP. Five of the compounds, A12B4C3, A1B4C3, A6B4C3, A26B11C2 and A39B1C2, were observed to cause significant inhibition as shown in FIG. 1C. Also shown are the data for three other compounds, A4B8C2, A28B3C1 and A24B12C3, as examples of the majority of compounds that failed to inhibit hPNKP. The chemical names and structures of these compounds are shown in FIG. 2.

Confirmation of Inhibition of PNKP Phosphatase Activity

Figure 3:
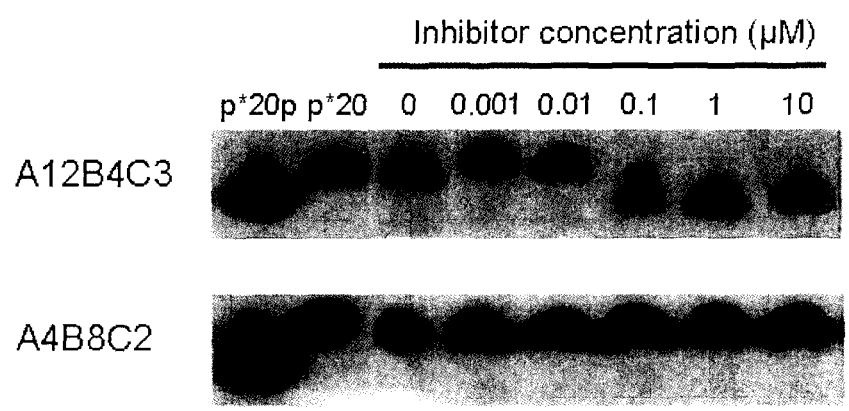
FIG. 3 depicts inhibition of hPNKP 3'-phosphatase activity using conventional radio-gel assay. A 20 mer oligonucleotide with a 3'-phosphate was labelled at the 5'-terminus with [γ-$^{32}$P]ATP (*p20p), which is acted on by hPNKP, resulting in the removal of the 3'-phosphate. This produces *p20 which has a slower mobility in the gel. Addition of the small molecule inhibitors reduces the conversion of *p20p to *p20.

A conventional radio-gel assay was used to verify the inhibition of hPNKP phosphatase activity by these small molecules. This assay shows a shift on an acrylamide sequencing gel that corresponds to 3'-phosphate removal from a 20-mer single-stranded oligonucleotide (35). Examples of the assay are shown in FIG. 3. All five of the positively identified compounds, namely A12B4C3, A1B4C3, A6B4C3, A26B11C2 and A39B1C2, inhibited hPNKP phosphatase activity. A number of small molecules shown by the screening assay not to be inhibitors of hPNKP phosphatase activity was also examined, and they also failed to show inhibition by the radio-gel approach (data not shown)

Inhibitory Activity and Specificity of A12B4C3

Figure 4:
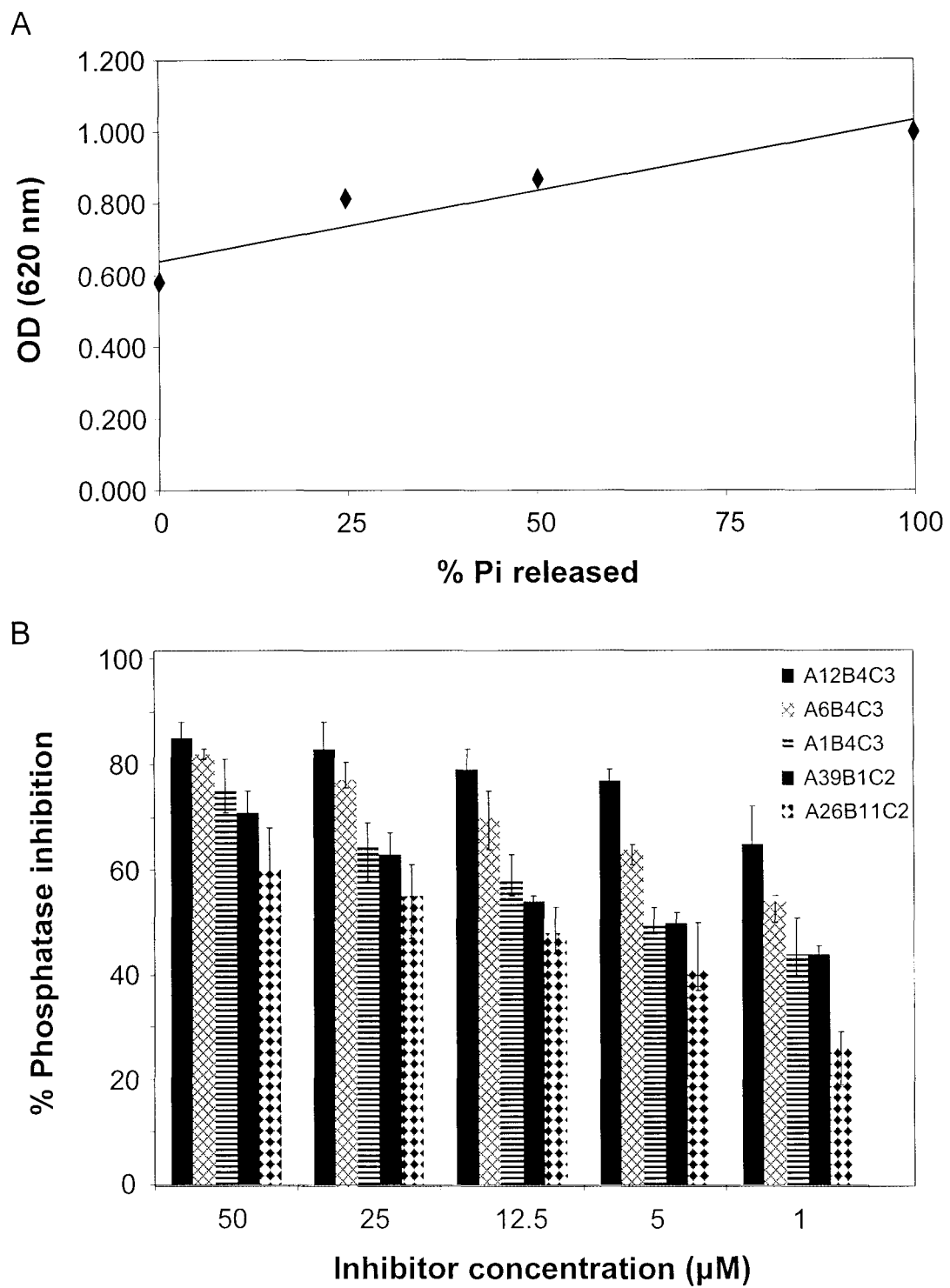
FIG. 4 depicts the measurement of 3'-phosphatase activity by the PiColorlock Gold assay. (Panel A) depicts a typical standard curve generated by mixing specific ratios of 3'-phosphorylated and non-phosphorylated 20 mer oligonucleotides (final concentration of oligonucleotide=100 µM) in 4 separate tubes, which were then treated with hPNKP for 30 minutes at 37° C., conditions that lead to complete 3'-dephosphorylation of the oligonucleotide. (Panel B) depicts concentration dependence of phosphatase inhibition by the five identified compounds. The data are drawn from 3 independent assays. Error bars indicate the S.E.M. (Panel C) depicts determination of the $IC_{50}$ values of the two most potent inhibitory compounds derived from 3 independent assays. The curves were fitted using GraphPad Prism software (GraphPad Software Inc., La Jolla, Calif.)
Figure 4:
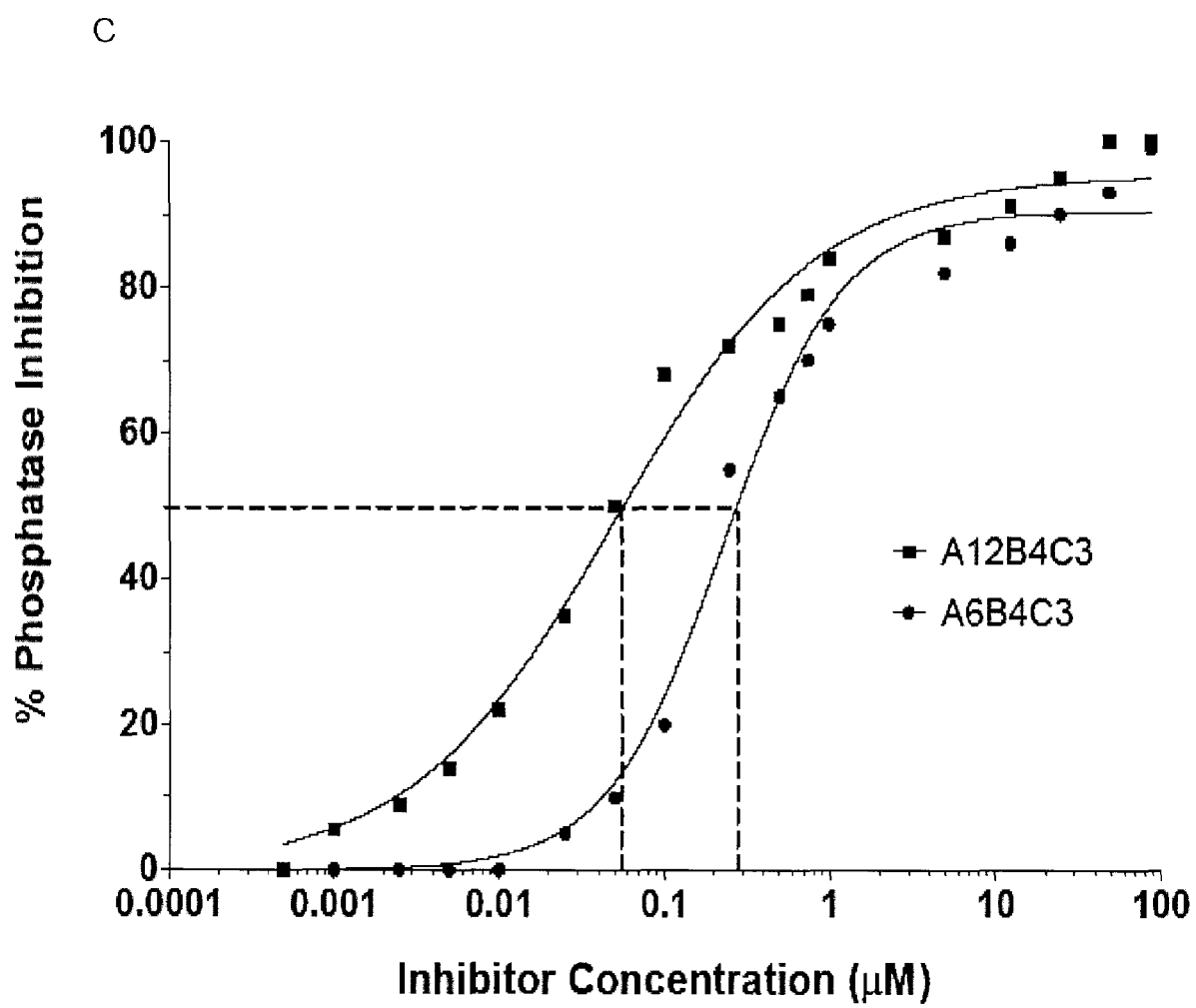

To further assess the activity of the five inhibitory molecules a proprietary colorimetric reagent (PiColorLock Gold) was used that measures release of inorganic phosphate. A drawback encountered with the fluorescence-based approach can be fluorescence quenching arising from direct interaction of the small molecule with the sensor agent. (Note in FIG. 1C the lower fluorescence signal of the sensor caused by exposure to some compounds in the absence of PNKP). This problem is avoided in the colorimetric assay, which measures the release of inorganic phosphate (Pi) from a 3'-phosphorylated 20-mer oligonucleotide based on the change in absorbance of malachite green in the presence of molybdate. Based on the standard curve obtained using 0, 25, 50, and 100% phosphorylated substrates (FIG. 4A), it was found that A12B4C3 was the most potent of the five PNKP inhibitors (FIG. 4B) and obtained an $IC_{50}$ dose of 0.06 µM and near maximal inhibition with a concentration of 5 µM (FIG. 4C). $IC_{50}$ values for the other compound, which also contains a nitrobenzylamine side chain, A6B4C3, was determined and found to be somewhat higher (~0.3 µM).

Specificity of A12B4C3

To determine the specificity of A12B4C3 for human PNKP phosphatase activity, a number of closely related phosphatases such as the PNKP enzymes isolated from bacteriophage T4, *Schizosaccharomyces pombe* and mouse, as well as aprataxin, were examined. It was observed that 50 µM A12B4C3 inhibited phage T4 and the *S. pombe* PNKPs by ~12.5 and ~20%, respectively, compared to ~85% inhibition of human PNKP (FIG. 5A). The compound significantly inhibited mouse PNKP (which shares ~80% identity to human PNKP) at all concentrations tested (down to 5 µM), though not quite as effectively as human PNKP (FIG. 5B).

Figure 5C:
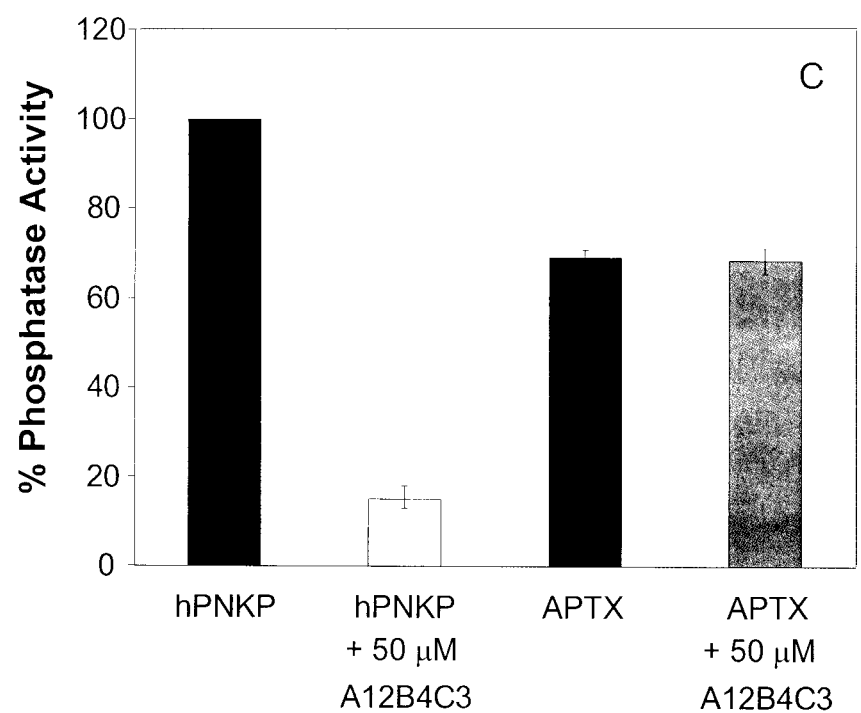
FIG. 5 depicts specificity of inhibition by A12B4C3. (Panel A) depicts inhibition of T4 PNK and fission yeast PNKP by 50 µM A12B4C3 measured by the PiColorLock assay. (Panel B) depicts a comparison of dose dependence of inhibition of mouse and human PNKPs by A12B4C3 measured by the PiColorLock assay. (Panel C) depicts a comparison of the 3'-DNA phosphatase activities of hPNKP and aprataxin (APTX) in the absence and presence of A12B4C3. The oligonucleotide substrate was incubated with equal quantities of the two enzymes that were purified on the same day. (Panel D) depicts the influence of A12B4C3 on protein phosphatases, which was examined as described in Material and Methods. No inhibition by A12B4C3 of PP-1 or calcineurin (CaN) was observed. In comparison microcystin LR (12 nM) inhibited PP-1. (Panel E) depicts dose-dependent inhibition of hPNKP DNA kinase activity by A12B4C3 measured by the transfer of radiolabeled phosphate from [γ-$^{32}$P] ATP as described in Materials and Methods. Data for each figure was compiled from 3 independent assays for each activity measured. The error bars show the S.E.M.

It was also tested whether A12B4C3 could inhibit aprataxin, which is another human DNA 3'-phosphatase. For this experiment, the oligonucleotide substrate was incubated with equal quantities of the two enzymes that were purified from bacteria on the same day. It was observed that aprataxin has a robust phosphatase activity that was refractory to 50 µM A12B4C3 (FIG. 5C).

Figure 5D:
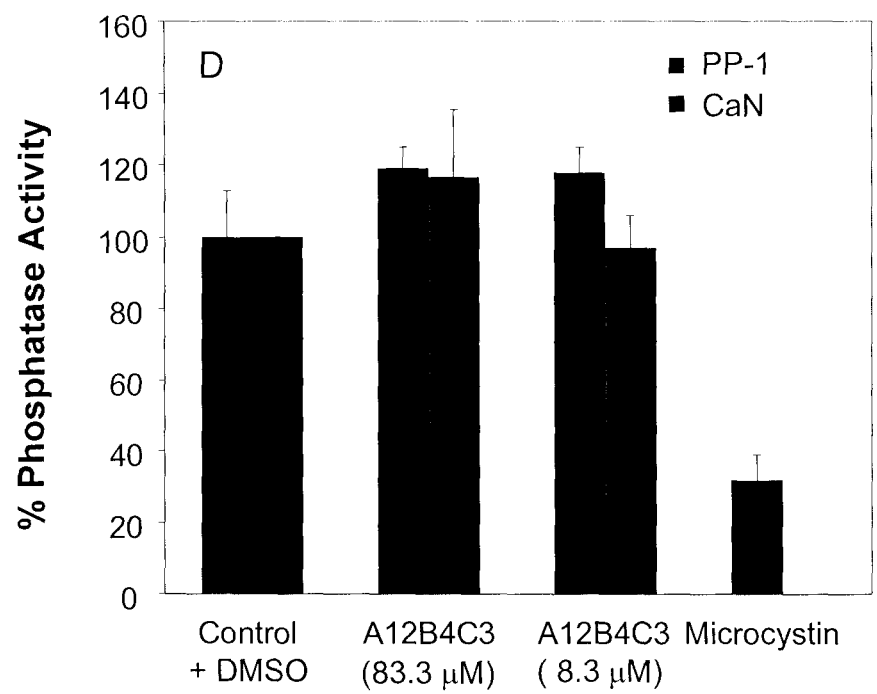
Figure 5:
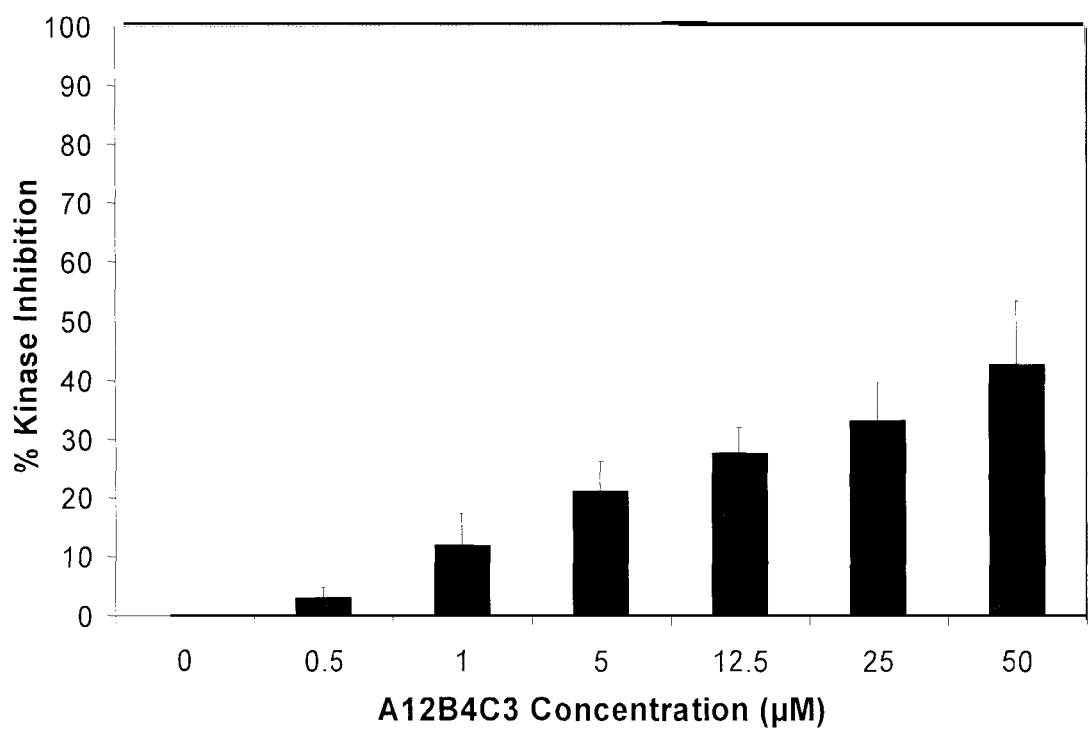

Two well known protein phosphatases, calcineurin and PP-1γ were also examined. Neither enzyme displayed inhibition when treated with an A12B4C3 concentration as high as 83.3 µM, whereas the control inhibitor microcystin LR reduced the activity of PP1 ~65% (FIG. 5D).

The effect of A12B4C3 on the kinase activity of human PNKP was examined by quantifying the transfer of $^{32}$P-labeled phosphate from radiolabeled ATP to an oligonucleotide. As shown in FIG. 5E, 50 µM A12B4C3 reduced human PNKP activity by ~30% but at 1 µM the inhibition was reduced to ~16%. However, the inhibition of the kinase and phosphatase activities cannot be directly compared because the standard assay for kinase activity uses ten-fold more enzyme than the assay for phosphatase activity Cytotoxicity of A12B4C3 and Cellular Radio-Sensitization and Chemo-Sensitization by A12B4C3

The foregoing data indicated that A12B4C3 is a potent inhibitor of human PNKP in vitro. The compound's effectiveness as a radiosensitizer was examined.

Figure 6:
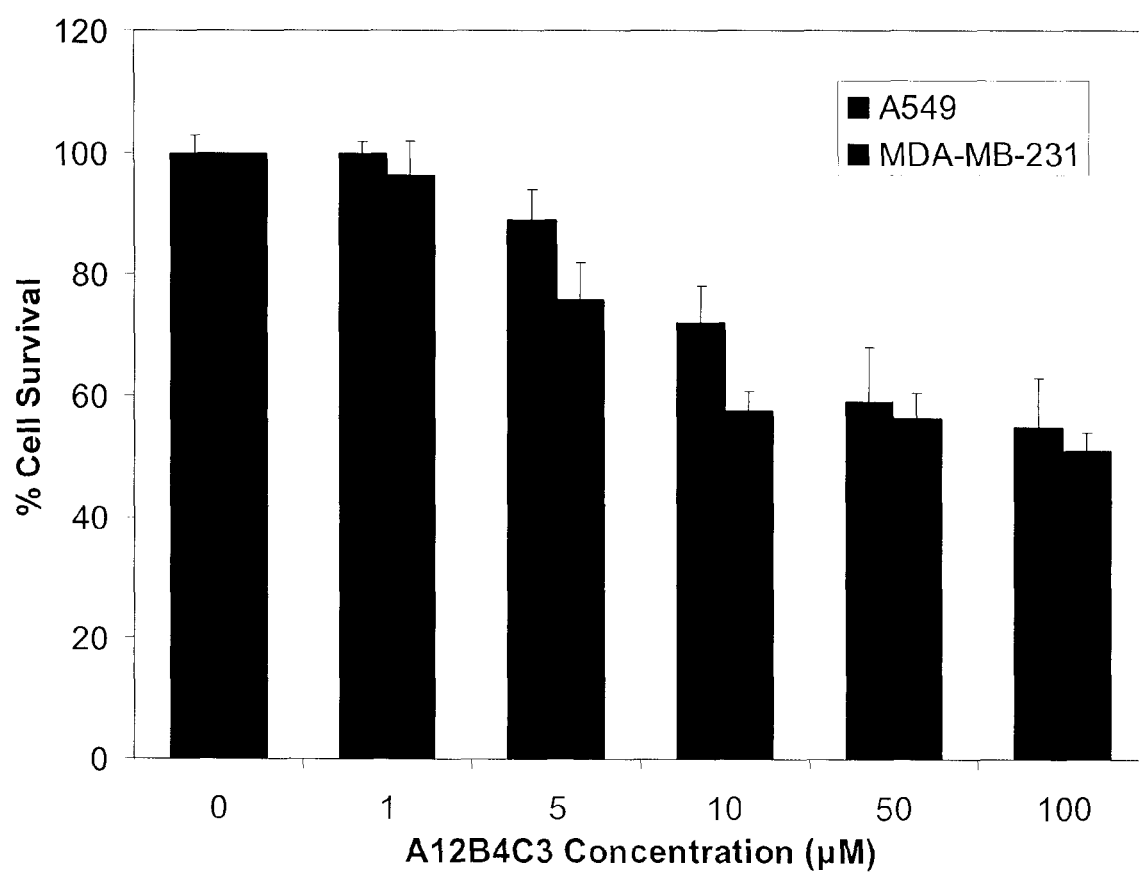
FIG. 6 depicts radiosensitization by A12B4C3. (Panel A) depicts cytotoxicity of A12B4C3 alone measured by 72-hour exposure of A549 lung cancer cells and MDA-MB-231 cells to increasing concentrations of the compound and determination of cell proliferation as described in Materials and Methods. The data are drawn from 3 independent determinations±S.E.M. (Panel B) depicts the influence of A12B4C3 on the radiosensitivity of wild-type A549 cells and PNKP-deficient cells (A549δPNKP). Cells were exposed to 1 µM A12B4C3 two hours prior to irradiation and then maintained in the same media for a further 24 hours. The media was then replaced with fresh media without the drug. Cytotoxicity was determined by the colony forming assay as described in Materials and Methods. The survival curves (±S.E.M.) are based on 4 independent sets of determinations. (Panel C) depicts the influence of A12B4C3 on the radiosensitivity of wild type MDA-MB-231 cells and PNKP-depleted MDA-MB-231 cells (MDA-MB-231δPNKP) using identical conditions to those described in FIG. 6B. The survival curves (±S.E.M.) are based on 5 independent sets of determinations.

A12B4C3 was first tested for inherent toxicity. Cytotoxicity was measured by cell proliferation assay after exposure of A549 human lung adenocarcinoma cells and MDA-MB-231 cells to different doses of the compound for 72 hours (FIG. 6A). A dose-dependent reduction in cell proliferation up to 50% at 100 µM A12B4C3 was observed. No further decrease was seen at higher doses. While not wishing to be bound by theory, this may be indicative of a maximal level of drug uptake. No effect on cell proliferation was detected after exposure to 1 µM A12B4C3. The lack of cytotoxicity at this dose was confirmed by clonogenic survival assay following exposure to A12B4C3 up to 24 hours (data not shown).

The capacity of A12B4C3 to act as a radiosensitizer was then examined. A549 cells were incubated with 1 µM A12B4C3 for 2 hours prior to irradiation and then maintained in the presence of the compound for a further 24 hours. The survival curves indicated that exposure to A12B4C3 almost doubled the radiosensitivity of A549 cells (FIG. 6B). This radiation response was nearly identical to that seen with cells depleted of PNKP by stable expression of shRNA (A549δPNKP). On the other hand, A12B4C3 failed to sensitize the PNKP-depleted cells. Similar data were obtained with wild type and PNKP-depleted MDA-MB-231 breast cancer cells (FIG. 6C).

The capacity of A12B4C3 to act as a chemosensitizer was then examined. A549 and A549δ PNKP cells were seeded on 60-mm tissue culture plates at various concentrations to give between about 100-1000 colonies per plate and returned to the incubator overnight to allow the cells to attach. The cells were incubated with or without 1 mM A12B4C3 for 2 hours before addition of camptothecin and then exposed to increasing doses of camptothecin (Sigma). After addition of camptothecin, cells were incubated for a further 24 hours in the same media and then washed twice with phosphate-buffered saline (PBS) and incubated in fresh media without the inhibitor. Colonies were stained with crystal violet after 10 to 14 days and counted with an automated Colcount colony counter (Oxford Optronix, Oxford, UK).

Discussion

The increased interest in therapeutics based on DNA repair inhibition has led to the discovery of several small molecule inhibitors of key DNA repair proteins including MGMT, PARP, ATM, DNA-PK, APE1, and Tdp1 (1, 4-6). Reduction in the activity of each of these enzymes sensitizes cells to a selection of chemotherapeutic agents and, in some cases, ionizing radiation. Previous studies suggested that PNKP depletion, mediated by shRNA, sensitizes cells to ionizing radiation, camptothecin and the alkylating agent, methyl methanesulphonate (24).

PNKP possesses 5'-kinase and 3'phosphatase activity. This necessitated the development of a suitable screening assay for inhibitors of the phosphatase activity. Most fluorescence-based high throughput screening assays for phosphatase activity have been directed towards protein phosphatases and rely on immunodetection using antibodies to the phosphorylated peptide substrate. The superquenching assay, originally devised by Rininsland et al. (34), presented an alternative approach that depended on the presence of a phosphate group for chemical recognition. It required some optimization involving protonation of the substrate to enhance the influence of the terminal phosphomonoester group over the internucleotide phosphodiester groups of the DNA substrate. Using this protocol a Z-factor of 0.68 was obtained, which is considered sufficient for identification of inhibitors in high throughput screens. The inhibitory activity of compounds identified by the superquenching assay was corroborated by the conventional radio-gel assay and by the PiColorlock colorimetric assay.

The chemical library of polysubstituted piperidines proved a relatively rich source of inhibitory compounds. The three most active compounds contain a nitrobenzylamine substituent on the ring nitrogen of the six membered ring of the piperidine (FIG. 2). The importance of this substituent to the binding of the inhibitor to PNKP remains to be determined. Of the three compounds, A12B4C3 was the most effective inhibitor of PNKP with an $IC_{50}$ of 0.5 µM compared to ~1 µM for the other two compounds (FIG. 4C). In addition to the nitrobenzyl substituent, A12B4C3 also features a long hydrophobic alkyl chain.

An important issue with all small molecule inhibitors is their specificity. The response of a number of other phosphatases to A12B4C3 was examined. Phage T4 polynucleotide kinase and human PNKP share similar nucleic acid kinase and phosphatase activities. However, with the exception of the enzyme active sites, the proteins bear no recognizable homology (25, 27). The phosphatase domains of both proteins belong to the haloacid dehalogenase (HAD) superfamily (25, 36, 37) with a conserved DxDGT motif, where the first Asp forms a covalent phospho-aspartate intermediate with the substrate. While not wishing to be bound by theory, that A12B4C3 failed to inhibit T4 PNK (FIG. 5A) suggests that the small molecule does not directly interact with this conserved HAD motif. The catalytic domain (phosphatase and kinase) of *S. pombe* PNKP, on the other hand, shares considerably more structural similarity with human PNKP than the T4 enzyme, with 127 identical residues, including the HAD motif (30). Despite this level of sequence overlap, the inhibition of *S. pombe* PNKP by A12B4C3 was limited (~20%), even at 50 μM inhibitor concentration (FIG. 5A). Again, while not wishing to be bound by theory, this may suggest that the compound interacts primarily with a region specific to mammalian PNKP, hence the strong inhibition of human and mouse PNKP (FIG. 5B).

A12B4C3 displayed no inhibition (FIG. 5D) of either of the two protein phosphatases tested, protein phosphatase 1 (PP-1) and calcineurin (protein phosphatase 2B), which are members of the eukaryotic serine/threonine family involved in a broad range of signal transduction pathways (38).

The possibility that A12B4C3 interacts with other protein phosphatases or indeed other enzymes can not be ruled out, but the tests for radiosensitization by A12B4C3 (FIGS. 6B and C) indicated not only that the compound effectively sensitized wild type cells to ionizing radiation, but also revealed that PNKP is most likely the cellular target for A12B4C3 in human cells because it failed to sensitize the PNKP-deficient cells.

Figure 7:
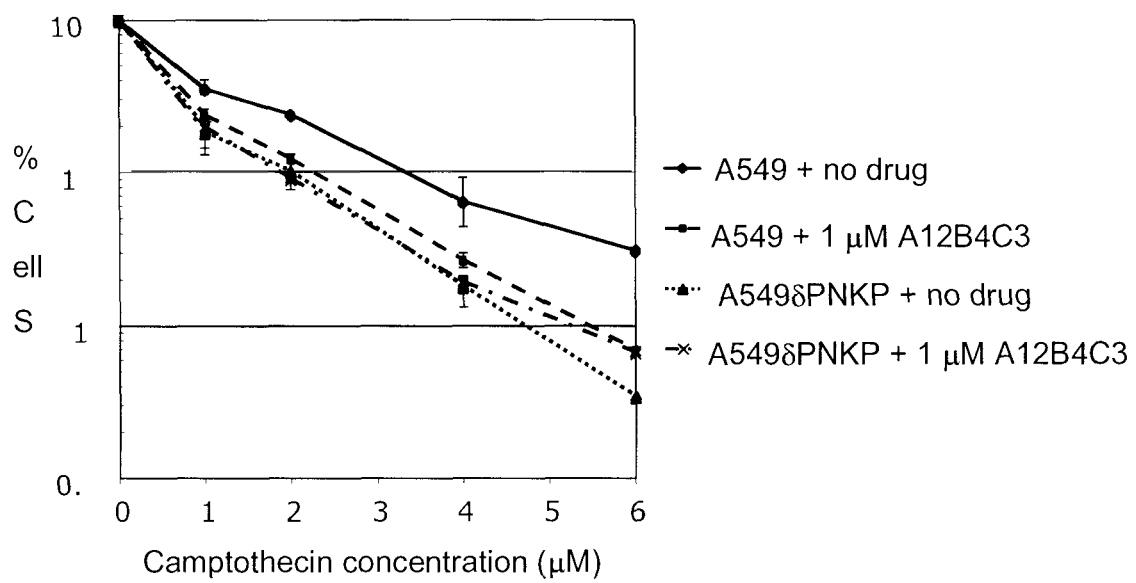
FIG. 7 is a graph depicting cell survival for A549 and A549δPNKP cells with Camptothecin +/−A12B4C3.
Figure 8:
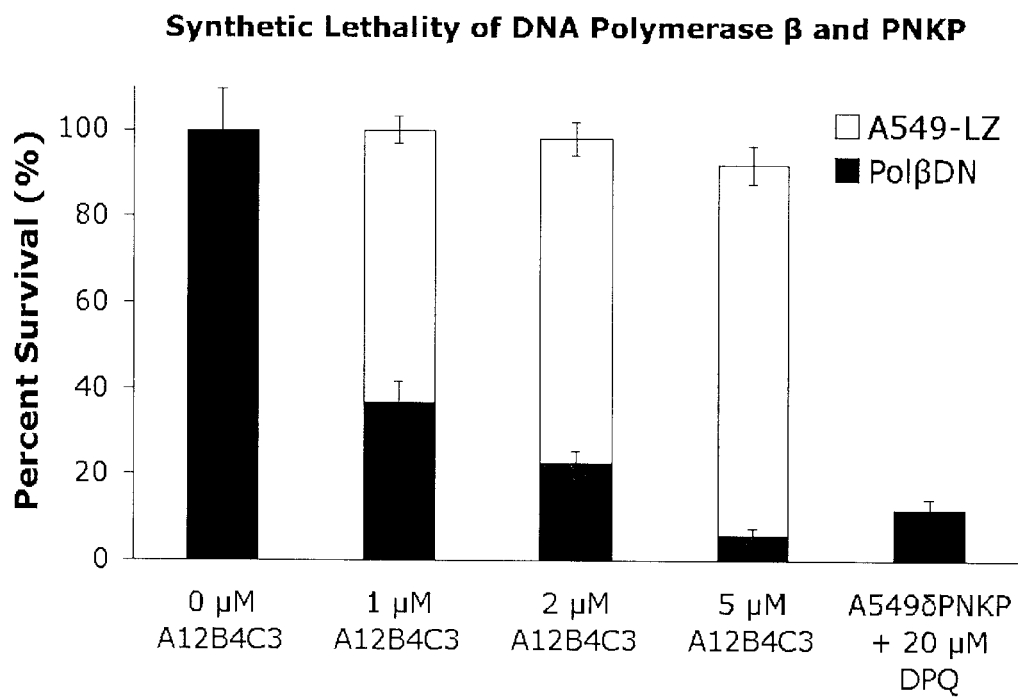
FIG. 8 is a graph depicting synthetic lethality of DNA polymerase β and PNKP. A) there is an inverse relationship between the concentration of PNKP inhibitor A12B4C3 and cell survival, indicating that co-disruption of DNA polymerase p and PNKP is synthetically lethal. PolβDN=A549 cells stably expressing a dominant negative form of DNA polymerase β. This vector encodes only the DNA binding domain of DNA polymerase β and not the catalytic domain, thereby acting as a dominant negative towards endogenous DNA polymerase β. A12B4C3=PNKP inhibitor and A549-LZ=A549-vector only cells and were used as our negative control. A549δPNKP cells are shown to be synthetically lethal with the PARP inhibitor DPQ and were used as the positive control. The data shown here is the average of six individual cell proliferation experiments where cell survival was determined by measuring fluorescence after addition of 10% v/v of Resazurin and incubation at 37° C. for 50 mins. Error bars were generated using the standard error of the mean.
Figure 9:
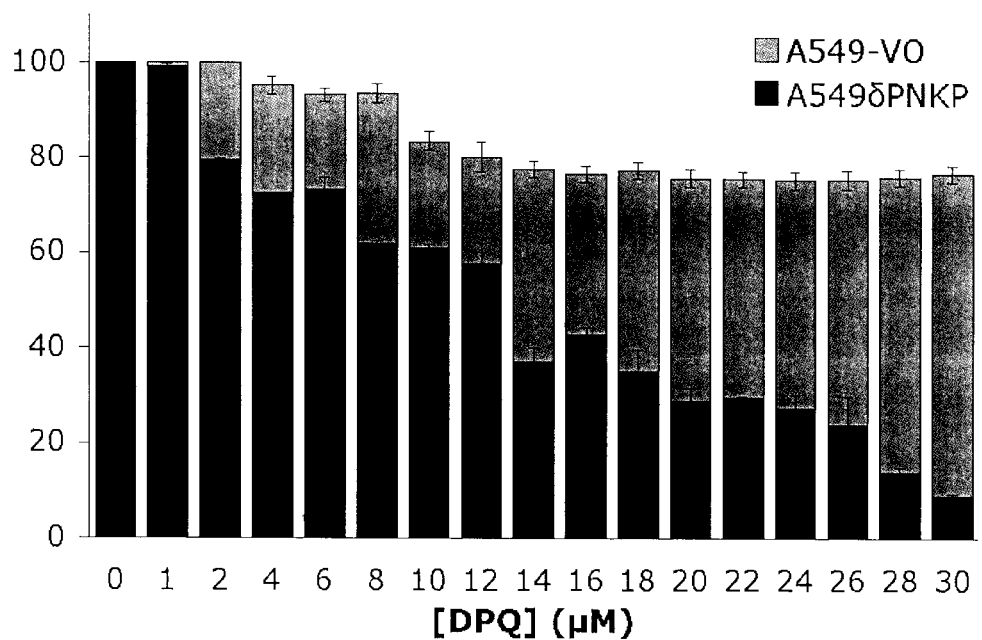
FIG. 9 is a graph depicting synthetic lethality of PNKP and PAR?. A549-VO=A549 vector only control cells and A549δPNKP=A549 cells in which PNKP has been stably knocked-down. Values represented here are an average of no less than four independent cell proliferation experiments where cell survival was determined as described in FIG. 8. Error bars were calculated using standard error of the mean. There is an inverse relationship between the concentration of the PARP inhibitor 3,4-dihydro-5[4-(1-piperindinyl)butoxy]-1(2H)-isoquinoline (DPQ) and cell survival of cells depleted of PNKP, however, there is no such relationship when comparing to control cells. This indicates that the co-disruption of PARP and PNKP causes synthetic lethality.

The tests for chemosensitization by A12B4C3 (FIG. 7) indicated that the compound effectively sensitized wild type cells to camptothecin.

EXAMPLE-II

Materials and Methods

Referring to FIGS. 8-11, to examine synthetic lethality, a 3-(4,5-dimethylthiazol-2-yl)-5-(3-carboxymethoxyphenyl)-2-(4-sulfophenyl)-2H-tetrazolium (MTS) fluorescence-based cell proliferation assay was used together with cell lines depleted of specific DNA repair proteins using shRNA, small molecule inhibitors of DNA repair proteins, or expression of dominant negative fragments of repair proteins.

Typically, 2,500 A549, Clone 13 (polynucleotide kinase/phosphatase (PNKP) depleted), DNA Polymerase βDominant Negative (Pol β DN), M059J (non-functional DNA-dependent protein kinase (DNA-PK)), or M059K (functional DNA-PK) cell lines were plated in a 96-well plate in 200 μL DMEM/F12 media.

A549 cells are a human lung adenocarcinoma cell line from ATCC. The DNA polymerase beta dominant negative A549 cells were provided by Drs Adrian Begg and Conchita Vens (Department of Experimental Therapy, The Netherlands Cancer Institute, Amsterdam, The Netherlands) [C. Vens, E. Dahmen-Mooren, M. Verwijs-Janssen, W. Blyweert, L. Graversen, H. Bartelink and A. C. Begg (2002) The role of DNA polymerase beta in determining sensitivity to ionizing radiation in human tumor cells, Nucleic Acids Res. 30:2995-3004]. M059J and M059K human glioma cell lines were provided by Dr. Joan Turner (Cross Cancer Institute) [Allalunis-Turner M J, Barron G M, Day R S 3rd, Dobler K D, Mirzayans R. (1993) Isolation of two cell lines from a human malignant glioma specimen differing in sensitivity to radiation and chemotherapeutic drugs. Radiation Research 134: 349-354].

The plate was then incubated at 37° C. for 24 hours. 3,4-dihydro-5[4-(1-piperindinyl)butoxy]-1(2H)-isoquinoline (DPQ) or A12B4C3 (also referred to as H5 herein, and in the Figures), was then added to the plates in varying concentrations. DPQ and A12B4C3 (also referred to as H5 herein, and in the Figures) are PARP and PNKP inhibitors, respectively.

The plate was then incubated at 37° C. for 72 hours. 15 μL of cell titer solution was then added to each of the wells and incubated at 37° C. for 4 hours. The cell titer solution contains an MTS compound that is reduced to a formazan product in active cells. The absorbance can then be measured at 490 nm using the FluoStar Optima machine.

Results and Discussion

Figure 10:
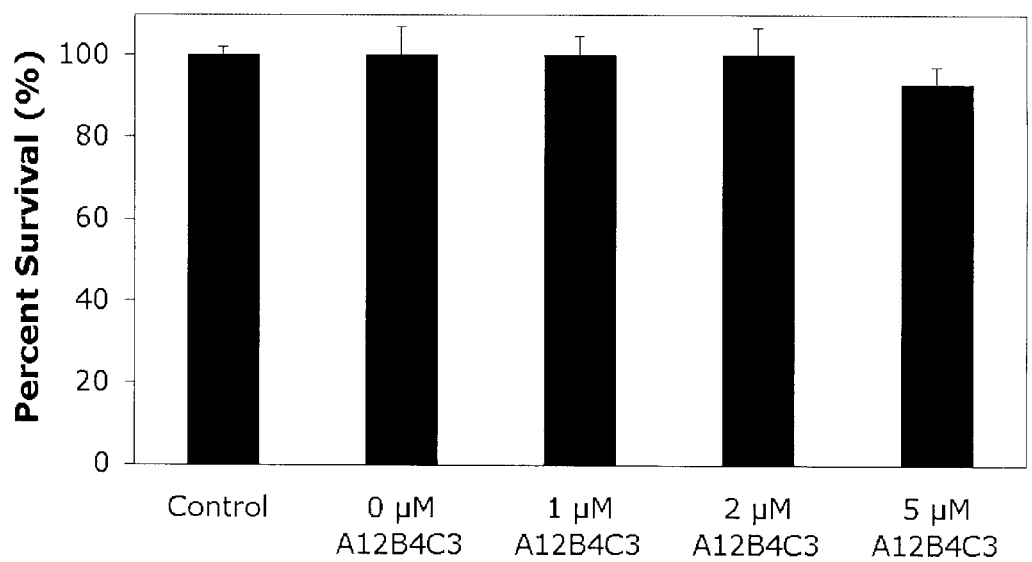
FIG. 10 is a graph depicting the lack of synthetic lethality between PNKP and DNA-PK. This graph shows that when M059J cells (DNA-PKcs negative) are subjected to increasing concentrations of A12B4C3, no synthetic lethality is seen. This data shows that co-disruption of PNKP and DNA-PK does not cause synthetic lethality. Values represented here are an average of no less than four independent cell proliferation experiments where cell survival was determined as described in FIG. 8.
Figure 11:
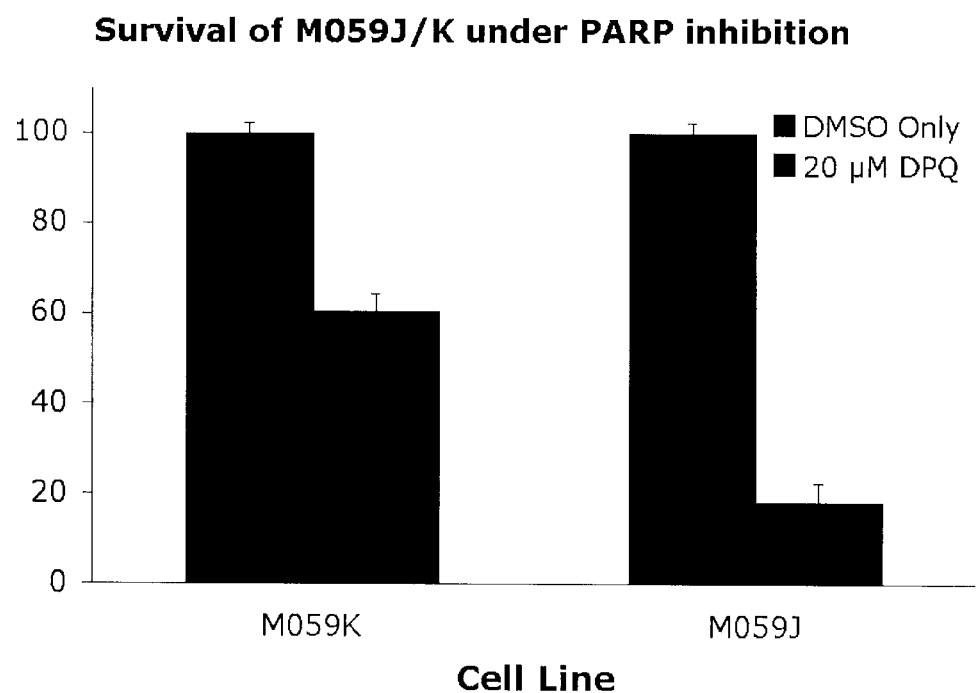
FIG. 11 is a graph depicting synthetic lethality of PARP and DNA-PK and demonstrates that when M059J (DNA-PKcs negative) and M059K (DNA-PKcs positive) cells are subjected to PARP inhibition using DPQ there is an apparent synthetically lethal relationship between DNA-PK and PARP (~3:1 ratio of survival between M059K and M059J cells when subjected to PARP inhibition). Values represented here are an average of no less than four independent cell proliferation experiments where cell survival was determined as described in FIG. 8.

Using the cell proliferation assay, it was determined that human PNKP is synthetically lethal with PARP (FIG. 9) and DNA polymerase β (Pol β) (FIG. 8), but not with DNA-PK (FIG. 10). It was also shown that DNA-PK is synthetically lethal with PARP (FIG. 11).

The results herein are consistent with PARP being synthetically lethal with proteins involved in DSB repair, PNKP and DNA-PK. Similarly, the SSB repair protein Pol is synthetically lethal with PNKP. However, the combination of DNA-PK and PNKP depletion did not show synthetic lethality.

REFERENCES

1. Madhusudan S, Middleton M R. The emerging role of DNA repair proteins as predictive, prognostic and therapeutic targets in cancer. Cancer Treat Rev 2005; 31: 603-17.
2. O'Connor M J, Martin N M, Smith G C. Targeted cancer therapies based on the inhibition of DNA strand break repair. Oncogene 2007; 26: 7816-24.
3. Drew Y, Calvert H. The potential of PARP inhibitors in genetic breast and ovarian cancers. Ann N Y Acad Sci 2008; 1138: 136-45.
4. Madhusudan S, Smart F, Shrimpton P, et al. Isolation of a small molecule inhibitor of DNA base excision repair. Nucleic Acids Res 2005; 33: 4711-24.
5. Marchand C, Lea W A, Jadhav A, et al. Identification of phosphotyrosine mimetic inhibitors of human tyrosyl-DNA phosphodiesterase I by a novel AlphaScreen high-throughput assay. Mol Cancer Ther 2009; 8: 240-8.
6. Hickson I, Zhao Y, Richardson C J, et al. Identification and characterization of a novel and specific inhibitor of the ataxia-telangiectasia mutated kinase ATM. Cancer Res 2004; 64: 9152-9.
7. Zhao Y, Thomas H D, Batey M A, et al. Preclinical evaluation of a potent novel DNA-dependent protein kinase inhibitor NU7441. Cancer Res 2006; 66: 5354-62.
8. Plummer R, Jones C, Middleton M, et al. Phase I study of the poly(ADP-ribose) polymerase inhibitor, AG014699, in combination with temozolomide in patients with advanced solid tumors. Clin Cancer Res 2008; 14: 7917-23.
9. Henner W D, Rodriguez L O, Hecht S M, Haseltine W A. gamma Ray induced deoxyribonucleic acid strand breaks. 3' Glycolate termini. J Biol Chem 1983; 258: 711-3.
10. Lennartz M, Coquerelle T, Bopp A, Hagen U. Oxygen—effect on strand breaks and specific end-groups in DNA of irradiated thymocytes. Int J Radiat Biol Relat Stud Phys Chem Med 1975; 27: 577-87.
11. Friedberg E C, Walker G C, Siede W, Wood R D, Schultz R A, Ellenberger T. DNA Repair and Mutagenesis. 2nd ed. Washington, D.C.: ASM Press; 2006.
12. Krokan H E, Nilsen H, Skorpen F, Otterlei M, Slupphaug G. Base excision repair of DNA in mammalian cells. FEBS Lett 2000; 476: 73-7.
13. Jilani A, Ramotar D, Slack C, et al. Molecular cloning of the human gene, PNKP, encoding a polynucleotide kinase 3'-phosphatase and evidence for its role in repair of DNA strand breaks caused by oxidative damage. J Biol Chem 1999; 274: 24176-86.
14. Karimi-Busheri F, Daly G, Robins P, et al. Molecular characterization of a human DNA kinase. J Biol Chem 1999; 274: 24187-94.
15. Whitehouse C J, Taylor R M, Thistlethwaite A, et al. XRCC1 stimulates human polynucleotide kinase activity at damaged DNA termini and accelerates DNA single-strand break repair. Cell 2001; 104: 107-17.
16. Loizou J I, El-Khamisy S F, Zlatanou A, et al. The protein kinase CK2 facilitates repair of chromosomal DNA single-strand breaks. Cell 2004; 117: 17-28.
17. Mani R S, Fanta M, Karimi-Busheri F, et al. XRCC1 stimulates polynucleotide kinase by enhancing its damage discrimination and displacement from DNA repair intermediates. J Biol Chem 2007; 282: 28004-13.
18. Chappell C, Hanakahi L A, Karimi-Busheri F, Weinfeld M, West S C. Involvement of human polynucleotide kinase in double-strand break repair by non-homologous end joining. Embo J 2002; 21: 2827-32.
19. Koch C A, Agyei R, Galicia S, et al. Xrcc4 physically links DNA end processing by polynucleotide kinase to DNA ligation by DNA ligase IV. Embo J 2004; 23: 3874-85.
20. Karimi-Busheri F, Rasouli-Nia A, Allalunis-Turner J, Weinfeld M. Human polynucleotide kinase participates in repair of DNA double-strand breaks by nonhomologous end joining but not homologous recombination. Cancer Res 2007; 67: 6619-25.
21. Wiederhold L, Leppard J B, Kedar P, et al. AP endonuclease-independent DNA base excision repair in human cells. Mol Cell 2004; 15: 209-20.
22. Das A, Wiederhold L, Leppard J B, et al. NEIL2-initiated, APE-independent repair of oxidized bases in DNA: Evidence for a repair complex in human cells. DNA Repair (Amst) 2006; 5: 1439-48.
23. Plo I, Liao Z Y, Barcelo J M, et al. Association of XRCC1 and tyrosyl DNA phosphodiesterase (Tdp1) for the repair of topoisomerase I-mediated DNA lesions. DNA Repair (Amst) 2003; 2: 1087-100.
24. Rasouli-Nia A, Karimi-Busheri F, Weinfeld M. Stable down-regulation of human polynucleotide kinase enhances spontaneous mutation frequency and sensitizes cells to genotoxic agents. Proc Natl Acad Sci USA 2004; 101: 6905-10.
25. Bernstein N K, Williams R S, Rakovszky M L, et al. The molecular architecture of the mammalian DNA repair enzyme, polynucleotide kinase. Mol Cell 2005; 17: 657-70.
26. Dobson C J, Allinson S L. The phosphatase activity of mammalian polynucleotide kinase takes precedence over its kinase activity in repair of single strand breaks. Nucleic Acids Res 2006; 34: 2230-7.
27. Bernstein N K, Karimi-Busheri F, Rasouli-Nia A, et al. Polynucleotide kinase as a potential target for enhancing cytotoxicity by ionizing radiation and topoisomerase I inhibitors. Anticancer Agents Med Chem 2008; 8: 358-67.
28. Ulaczyk-Lesanko A, Pelletier E, Lee M, Prinz H, Waldmann H, Hall D G. Optimization of three- and four-component reactions for polysubstituted piperidines: application to the synthesis and preliminary biological screening of a prototype library. J Comb Chem 2007; 9: 695-703.
29. Mani R S, Karimi-Busheri F, Fanta M, Cass C E, Weinfeld M. Spectroscopic studies of DNA and ATP binding to human polynucleotide kinase: evidence for a ternary complex. Biochemistry 2003; 42: 12077-84.
30. Meijer M, Karimi-Busheri F, Huang T Y, Weinfeld M, Young D. Pnk1, a DNA kinase/phosphatase required for normal response to DNA damage by gamma-radiation or camptothecin in *Schizosaccharomyces pombe*. J Biol Chem 2002; 277: 4050-5.
31. Misik A J, Perreault K, Holmes C F, Fliegel L. Protein phosphatase regulation of Na+/H+ exchanger isoform I. Biochemistry 2005; 44: 5842-52.
32. Wei Q, Lee E Y. Expression and reconstitution of calcineurin A and B subunits. Biochem Mol Biol Int 1997; 41: 169-77.
33. An J, Carmichael W W. Use of a colorimetric protein phosphatase inhibition assay and enzyme linked immunosorbent assay for the study of microcystins and nodularins. Toxicon 1994; 32: 1495-507.
34. Rininsland F, Xia W, Wittenburg S, et al. Metal ion-mediated polymer superquenching for highly sensitive detection of kinase and phosphatase activities. Proc Natl Acad Sci USA 2004; 101: 15295-300.
35. Karimi-Busheri F, Lee J, Tomkinson A E, Weinfeld M. Repair of DNA strand gaps and nicks containing 3'-phosphate and 5'-hydroxyl termini by purified mammalian enzymes. Nucleic Acids Res 1998; 26: 4395-400.
36. Aravind L, Koonin E V. The HD domain defines a new superfamily of metal-dependent phosphohydrolases. Trends Biochem Sci 1998; 23: 469-72.
37. Wang L K, Lima C D, Shuman S. Structure and mechanism of T4 polynucleotide kinase: an RNA repair enzyme. Embo J 2002; 21: 3873-80.
38. Villafranca J E, Kissinger C R, Parge H E. Protein serine/threonine phosphatases. Curr Opin Biotechnol 1996; 7: 397-402.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

The embodiments of the invention in which an exclusive property or privilege is claimed are defined as follows:

1. A pharmaceutical composition comprising: a first amount of a topoisomerase I inhibitor and a second amount of a polynucleotide kinase/phosphatase (PNKP) inhibitor, and a pharmaceutically acceptable carrier.

2. The pharmaceutical composition of claim 1, wherein said PNKP inhibitor is 2-(1-hydroxyundecyl)-1-(4-nitrophenylamino)-6-phenyl-6,7a-dihydro-1H-pyrrolo[3,4-b]pyridine-5,7(2H,4aH)-dione (A12B4C3), 2-(hydroxy(phenyl)methyl)-1-(4-nitrophenylamino)-6-phenyl-6,7a-dihydro-1Hpyrrolo[3,4-b]pyridine-5,7(2H,4aH)-dione (A1B4C3), 2-(hydroxy(3,4,5-trimethoxyphenyl)methyl)-1-(4-nitrophenylamino)-6-phenyl-6,7adihydro-1H-pyrrolo[3,4-b]pyridine-5,7(2H,4aH)-dione (A6B4C3), tert-butyl 2-(1-hydroxy-2,2-diphenylethyl)-6-methyl-5,7-dioxo-2,4-a,5,6,7,7a-hexahydro-1Hpyrrolo[3,4-b]pyridin-1-ylcarbamate A26B11C2) or 2-(hydroxy(thiophen-2-yl)methyl)-6-methyl-1-(phenylamino)-6,7a-dihydro-1Hpyrrolo[3,4-b]pyridine-5,7(2H,4aH)-dione (A39B1C2).

3. The pharmaceutical composition of claim 1, wherein said PNKP inhibitor is A12B4C3.

4. The pharmaceutical composition of claim 1, wherein said topoisomerase I inhibitor is gimatecan, irinotecan, or camptothecin.

5. The pharmaceutical composition of claim 4, wherein said topoisomerase I inhibitor is camptothecin.

6. The pharmaceutical composition of claim 1, wherein said PNKP inhibitor is A12B4C3 and said topoisomerase I inhibitor is camptothecin.

7. A combination comprising a topoisomerase I inhibitor and a polynucleotide kinase/phosphatase (PNKP).

8. The combination of claim 7, wherein said PNKP inhibitor is 2-(1-hydroxyundecyl)-1-(4-nitrophenylamino)-6-phenyl-6,7a-dihydro-1Hpyrrolo[3,4-b]pyridine-5,7(2H,4aH)-dione (A12B4C3), 2-(hydroxy(phenyl)methyl)-1-(4-nitrophenylamino)-6-phenyl-6,7a-dihydro-1Hpyrrolo[3,4-b]pyridine-5,7(2H,4aH)-dione (A1B4C3), 2-(hydroxy(3,4,5-trimethoxyphenyl)methyl)-1-(4-nitrophenylamino)-6-phenyl-6,7adihydro-1H-pyrrolo[3,4-b]pyridine-5,7(2H,4aH)-dione (A6B4C3), tert-butyl 2-(1-hydroxy-2,2-diphenylethyl)-6-methyl-5,7-dioxo-2,4-a,5,6,7,7a-hexahydro-1Hpyrrolo[3,4-b]pyridin-1-ylcarbamate A26B11C2) or 2-(hydroxy(thiophen-2-yl)methyl)-6-methyl-1-(phenylamino)-6,7a-dihydro-1Hpyrrolo[3,4-b]pyridine-5,7(2H,4aH)-dione (A39B1C2).

9. The combination of claim 7, wherein said PNKP inhibitor is A12B4C3.

10. The combination of claim 7, wherein said topoisomerase I inhibitor is gimatecan, irinotecan, or camptothecin.

11. The combination of claim 10, wherein said topoisomerase I inhibitor is camptothecin.

12. The combination of claim 7, wherein said PNKP inhibitor is A12B4C3 and said topoisomerase I inhibitor is camptothecin.

13. A method of treating a subject suffering from a disorder associated with a defect in DNA polymerase β, comprising administering to said subject an inhibitor of polynucleotide kinase/phosphatase (PNKP).

* * * * *